US010953307B2

(12) United States Patent
Wilson et al.

(10) Patent No.: US 10,953,307 B2
(45) Date of Patent: Mar. 23, 2021

(54) SWIM TRACKING AND NOTIFICATIONS FOR WEARABLE DEVICES

(71) Applicant: Apple Inc., Cupertino, CA (US)

(72) Inventors: James R. Wilson, Cupertino, CA (US); Christopher D. Jones, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/556,023

(22) Filed: Aug. 29, 2019

(65) Prior Publication Data

US 2020/0101365 A1 Apr. 2, 2020

Related U.S. Application Data

(60) Provisional application No. 62/739,133, filed on Sep. 28, 2018.

(51) Int. Cl.
| G08B 3/00 | (2006.01) |
| A63B 71/06 | (2006.01) |
| G08B 7/06 | (2006.01) |
| A63B 24/00 | (2006.01) |
| A61B 5/11 | (2006.01) |

(52) U.S. Cl.
CPC ...... *A63B 71/0622* (2013.01); *A63B 24/0062* (2013.01); *A63B 71/0686* (2013.01); *G08B 7/06* (2013.01); *A61B 5/1118* (2013.01); *A63B 2071/0655* (2013.01); *A63B 2071/0663* (2013.01); *A63B 2071/0694* (2013.01); *A63B 2230/75* (2013.01); *A63B 2244/20* (2013.01)

(58) Field of Classification Search
CPC .......... A63B 71/0622; A63B 24/0062; A63B 71/0686; G08B 7/06
See application file for complete search history.

(56) References Cited

U.S. PATENT DOCUMENTS

| 4,205,628 A | 6/1980 | Null |
| 4,842,266 A | 6/1989 | Sweeney et al. |
| 5,423,863 A | 6/1995 | Felblinger et al. |
| 5,788,655 A | 8/1998 | Yoshimura et al. |
| 6,013,008 A | 1/2000 | Fukushima |
| 6,095,949 A | 8/2000 | Arai |
| 6,095,984 A | 8/2000 | Amano et al. |

(Continued)

FOREIGN PATENT DOCUMENTS

| CA | 2815518 A1 | 5/2012 |
| CN | 1337638 A | 2/2002 |

(Continued)

OTHER PUBLICATIONS

Final Office Action received for U.S. Appl. No. 16/144,753, dated Sep. 22, 2020, 9 pages.

(Continued)

*Primary Examiner* — Phung Nguyen
(74) *Attorney, Agent, or Firm* — Dentons US LLP

(57) ABSTRACT

The present disclosure generally relates to providing perceptual notifications containing information about a measured activity-based value of a swim characteristic. In some examples, the perceptual notifications utilize colors and haptic taps to convey measured values of the swim characteristic without requiring the swimmer to interact with the perceptual notification while the swimmer is swimming.

39 Claims, 25 Drawing Sheets

(56) References Cited

U.S. PATENT DOCUMENTS

| | | | |
|---|---|---|---|
| 6,097,371 A | 8/2000 | Siddiqui et al. | |
| 6,244,988 B1 | 6/2001 | Delman | |
| 6,416,471 B1 | 7/2002 | Kumar et al. | |
| 6,603,477 B1 | 8/2003 | Tittle | |
| 6,639,584 B1 | 10/2003 | Li | |
| 6,705,972 B1 | 3/2004 | Takano et al. | |
| 6,837,827 B1 | 1/2005 | Lee et al. | |
| 6,866,613 B1 | 3/2005 | Brown et al. | |
| 7,128,693 B2 | 10/2006 | Brown et al. | |
| 7,251,454 B2 | 7/2007 | White | |
| 7,662,065 B1 | 2/2010 | Kahn et al. | |
| 7,739,148 B2 | 6/2010 | Suzuki et al. | |
| 8,105,208 B2 | 1/2012 | Oleson et al. | |
| 8,321,006 B1 | 11/2012 | Snyder et al. | |
| 8,341,557 B2 | 12/2012 | Pisula et al. | |
| 8,475,339 B2 | 7/2013 | Hwang et al. | |
| 8,676,170 B2 | 3/2014 | Porrati et al. | |
| 8,784,115 B1 | 7/2014 | Chuang | |
| 8,825,445 B2 | 9/2014 | Hoffman et al. | |
| 8,934,963 B1 | 1/2015 | Farazi | |
| 8,990,006 B1 | 3/2015 | Wallace et al. | |
| 9,020,538 B1 | 4/2015 | White et al. | |
| 9,224,291 B2 | 12/2015 | Moll-Carrillo et al. | |
| 9,557,881 B1 | 1/2017 | Jain et al. | |
| 9,589,445 B2 | 3/2017 | White et al. | |
| 9,712,629 B2 | 7/2017 | Molettiere et al. | |
| 9,734,477 B2 | 8/2017 | Weast et al. | |
| 9,813,642 B1 | 11/2017 | Chen et al. | |
| 9,817,481 B2 | 11/2017 | Pantelopoulos et al. | |
| 9,854,653 B1 | 12/2017 | Ackmann et al. | |
| 9,880,805 B1 | 1/2018 | Guralnick | |
| 9,940,682 B2 | 4/2018 | Hoffman et al. | |
| 10,300,334 B1* | 5/2019 | Chuang | G16H 50/30 |
| 10,304,347 B2 | 5/2019 | Wilson et al. | |
| 10,339,830 B2 | 7/2019 | Han et al. | |
| 10,398,381 B1 | 9/2019 | Heneghan et al. | |
| 10,777,314 B1 | 9/2020 | Williams et al. | |
| 2001/0049470 A1 | 12/2001 | Mault et al. | |
| 2002/0045960 A1 | 4/2002 | Phillips et al. | |
| 2002/0086774 A1 | 7/2002 | Warner | |
| 2002/0118121 A1 | 8/2002 | Lehrman et al. | |
| 2003/0023178 A1 | 1/2003 | Bischoff et al. | |
| 2003/0064860 A1 | 4/2003 | Yamashita et al. | |
| 2003/0182628 A1 | 9/2003 | Lira | |
| 2003/0216971 A1 | 11/2003 | Sick et al. | |
| 2003/0226695 A1 | 12/2003 | Mault | |
| 2004/0014567 A1 | 1/2004 | Mendel | |
| 2004/0077462 A1 | 4/2004 | Brown et al. | |
| 2004/0128286 A1 | 7/2004 | Yasushi et al. | |
| 2005/0075214 A1 | 4/2005 | Brown et al. | |
| 2005/0079905 A1 | 4/2005 | Martens | |
| 2005/0124324 A1 | 6/2005 | Thomas et al. | |
| 2005/0139852 A1 | 6/2005 | Chen et al. | |
| 2005/0172311 A1 | 8/2005 | Hjelt et al. | |
| 2005/0197063 A1 | 9/2005 | White | |
| 2005/0216867 A1 | 9/2005 | Marvit et al. | |
| 2005/0228735 A1 | 10/2005 | Duquette | |
| 2005/0272564 A1 | 12/2005 | Pyles et al. | |
| 2006/0020174 A1 | 1/2006 | Matsumura et al. | |
| 2006/0052727 A1 | 3/2006 | Palestrant | |
| 2006/0098109 A1 | 5/2006 | Ooki | |
| 2006/0106741 A1 | 5/2006 | Janarthanan | |
| 2006/0250524 A1 | 11/2006 | Roche | |
| 2007/0021269 A1 | 1/2007 | Shum | |
| 2007/0032733 A1 | 2/2007 | Burton | |
| 2007/0056727 A1 | 3/2007 | Newman | |
| 2007/0113726 A1 | 5/2007 | Oliver et al. | |
| 2007/0136093 A1 | 6/2007 | Rankin et al. | |
| 2007/0143433 A1 | 6/2007 | Daigle | |
| 2007/0249949 A1 | 10/2007 | Hadley | |
| 2007/0271065 A1 | 11/2007 | Gupta et al. | |
| 2008/0052945 A1 | 3/2008 | Matas et al. | |
| 2008/0058626 A1 | 3/2008 | Miyata et al. | |
| 2008/0076637 A1 | 3/2008 | Gilley et al. | |
| 2008/0086318 A1 | 4/2008 | Gilley et al. | |
| 2008/0096726 A1 | 4/2008 | Riley et al. | |
| 2008/0141135 A1 | 6/2008 | Mason et al. | |
| 2008/0150731 A1 | 6/2008 | Laukkanen et al. | |
| 2008/0161707 A1 | 7/2008 | Farringdon et al. | |
| 2008/0200312 A1 | 8/2008 | Tagliabue | |
| 2008/0300110 A1 | 12/2008 | Smith et al. | |
| 2009/0012988 A1 | 1/2009 | Brown | |
| 2009/0118100 A1* | 5/2009 | Oliver | A63B 24/0062 482/8 |
| 2009/0164567 A1 | 6/2009 | Hara | |
| 2009/0192823 A1 | 7/2009 | Hawkins et al. | |
| 2009/0210078 A1 | 8/2009 | Crowley | |
| 2009/0216556 A1 | 8/2009 | Martin et al. | |
| 2009/0222056 A1 | 9/2009 | Lindh et al. | |
| 2009/0233771 A1 | 9/2009 | Quatrochi et al. | |
| 2009/0262088 A1 | 10/2009 | Moll-carrillo et al. | |
| 2009/0287103 A1 | 11/2009 | Pillai | |
| 2009/0319243 A1 | 12/2009 | Suarez-rivera et al. | |
| 2010/0031202 A1 | 2/2010 | Morris et al. | |
| 2010/0042949 A1 | 2/2010 | Chen | |
| 2010/0048358 A1 | 2/2010 | Tchao et al. | |
| 2010/0060586 A1 | 3/2010 | Pisula et al. | |
| 2010/0062818 A1 | 3/2010 | Haughay et al. | |
| 2010/0062905 A1 | 3/2010 | Rottler et al. | |
| 2010/0064255 A1 | 3/2010 | Rottler et al. | |
| 2010/0076331 A1 | 3/2010 | Chan et al. | |
| 2010/0079291 A1 | 4/2010 | Kroll et al. | |
| 2010/0121700 A1 | 5/2010 | Wigder et al. | |
| 2010/0145209 A1 | 6/2010 | Lee et al. | |
| 2010/0179832 A1 | 7/2010 | Van deursen et al. | |
| 2010/0194692 A1 | 8/2010 | Orr et al. | |
| 2010/0198453 A1 | 8/2010 | Dorogusker et al. | |
| 2010/0281374 A1 | 11/2010 | Schulz et al. | |
| 2010/0292600 A1 | 11/2010 | Dibenedetto et al. | |
| 2010/0298899 A1 | 11/2010 | Donnelly et al. | |
| 2010/0305965 A1 | 12/2010 | Benjamin et al. | |
| 2010/0331145 A1 | 12/2010 | Lakovic et al. | |
| 2011/0003665 A1 | 1/2011 | Burton et al. | |
| 2011/0016120 A1 | 1/2011 | Haughay et al. | |
| 2011/0066051 A1 | 3/2011 | Moon et al. | |
| 2011/0071869 A1 | 3/2011 | Obrien et al. | |
| 2011/0074699 A1 | 3/2011 | Marr et al. | |
| 2011/0098928 A1 | 4/2011 | Hoffman et al. | |
| 2011/0112418 A1 | 5/2011 | Feild et al. | |
| 2011/0125041 A1 | 5/2011 | Fischell et al. | |
| 2011/0137678 A1 | 6/2011 | Williams | |
| 2011/0137836 A1 | 6/2011 | Kuriyama et al. | |
| 2011/0167369 A1 | 7/2011 | Van Os | |
| 2011/0213276 A1 | 9/2011 | Sarussi et al. | |
| 2011/0227872 A1 | 9/2011 | Huska et al. | |
| 2011/0230169 A1 | 9/2011 | Ohki | |
| 2011/0230986 A1 | 9/2011 | Lafortune et al. | |
| 2011/0246509 A1 | 10/2011 | Migita et al. | |
| 2011/0261079 A1 | 10/2011 | Ingrassia et al. | |
| 2011/0275940 A1 | 11/2011 | Nims et al. | |
| 2011/0306389 A1 | 12/2011 | Nagayama | |
| 2011/0307821 A1 | 12/2011 | Martens | |
| 2012/0015778 A1 | 1/2012 | Lee et al. | |
| 2012/0015779 A1 | 1/2012 | Powch et al. | |
| 2012/0030623 A1 | 2/2012 | Hoellwarth | |
| 2012/0034897 A1 | 2/2012 | Kreitzer et al. | |
| 2012/0041767 A1 | 2/2012 | Hoffman et al. | |
| 2012/0042039 A1 | 2/2012 | Mark | |
| 2012/0071770 A1 | 3/2012 | Grey et al. | |
| 2012/0092383 A1 | 4/2012 | Hysek et al. | |
| 2012/0105225 A1 | 5/2012 | Valtonen | |
| 2012/0116550 A1 | 5/2012 | Hoffman et al. | |
| 2012/0232414 A1 | 9/2012 | Mollicone et al. | |
| 2012/0253485 A1 | 10/2012 | Weast et al. | |
| 2012/0274508 A1 | 11/2012 | Brown et al. | |
| 2012/0317167 A1 | 12/2012 | Rahman et al. | |
| 2012/0326873 A1 | 12/2012 | Utter, II | |
| 2013/0054150 A1 | 2/2013 | Sacks et al. | |
| 2013/0054720 A1 | 2/2013 | Kang et al. | |
| 2013/0067050 A1 | 3/2013 | Kotteri et al. | |
| 2013/0081083 A1 | 3/2013 | Yu et al. | |
| 2013/0093715 A1 | 4/2013 | Marsden et al. | |
| 2013/0106603 A1 | 5/2013 | Weast et al. | |
| 2013/0106684 A1 | 5/2013 | Weast et al. | |

(56) References Cited

U.S. PATENT DOCUMENTS

| | | |
|---|---|---|
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0141233 A1 | 6/2013 | Jacobs et al. |
| 2013/0151285 A1 | 6/2013 | Mclaren et al. |
| 2013/0184613 A1 | 7/2013 | Homsi et al. |
| 2013/0187923 A1 | 7/2013 | Yoshimoto et al. |
| 2013/0188322 A1 | 7/2013 | Lowe |
| 2013/0197679 A1 | 8/2013 | Balakrishnan et al. |
| 2013/0198672 A1 | 8/2013 | Yoon et al. |
| 2013/0203475 A1 | 8/2013 | Kil et al. |
| 2013/0217979 A1 | 8/2013 | Blackadar et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0262155 A1 | 10/2013 | Hinkamp |
| 2013/0325394 A1 | 12/2013 | Yuen et al. |
| 2013/0325396 A1 | 12/2013 | Yuen et al. |
| 2013/0332286 A1 | 12/2013 | Medelius et al. |
| 2013/0345978 A1 | 12/2013 | Lush et al. |
| 2014/0038781 A1 | 2/2014 | Foley et al. |
| 2014/0067096 A1 | 3/2014 | Aibara |
| 2014/0081666 A1 | 3/2014 | Teller et al. |
| 2014/0108998 A1 | 4/2014 | Chaudhri et al. |
| 2014/0139637 A1 | 5/2014 | Mistry et al. |
| 2014/0176346 A1 | 6/2014 | Brumback et al. |
| 2014/0176475 A1 | 6/2014 | Myers et al. |
| 2014/0189584 A1 | 7/2014 | Weng et al. |
| 2014/0200691 A1 | 7/2014 | Lee et al. |
| 2014/0218369 A1 | 8/2014 | Yuen et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0275852 A1 | 9/2014 | Hong et al. |
| 2014/0275854 A1 | 9/2014 | Venkatraman et al. |
| 2014/0277628 A1* | 9/2014 | Nieminen .......... G06K 9/00342 700/91 |
| 2014/0278229 A1* | 9/2014 | Hong .................... A61B 5/486 702/160 |
| 2014/0282153 A1 | 9/2014 | Christiansen et al. |
| 2014/0288680 A1 | 9/2014 | Hoffman et al. |
| 2014/0336796 A1 | 11/2014 | Agnew |
| 2014/0337450 A1 | 11/2014 | Choudhary et al. |
| 2014/0337451 A1 | 11/2014 | Choudhary et al. |
| 2014/0344723 A1 | 11/2014 | Malik et al. |
| 2014/0371887 A1 | 12/2014 | Hoffman et al. |
| 2015/0018632 A1 | 1/2015 | Khair |
| 2015/0057943 A1 | 2/2015 | Self et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0118657 A1 | 4/2015 | Shrake et al. |
| 2015/0130830 A1 | 5/2015 | Nagasaki et al. |
| 2015/0142689 A1 | 5/2015 | Squires |
| 2015/0153943 A1 | 6/2015 | Wang |
| 2015/0181314 A1 | 6/2015 | Swanson |
| 2015/0185967 A1 | 7/2015 | Ly et al. |
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0217163 A1 | 8/2015 | Amis et al. |
| 2015/0220883 A1 | 8/2015 | B'far et al. |
| 2015/0269848 A1 | 9/2015 | Yuen et al. |
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0347711 A1 | 12/2015 | Soli et al. |
| 2015/0374310 A1 | 12/2015 | Lee |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0065505 A1 | 3/2016 | Iskander |
| 2016/0085937 A1 | 3/2016 | Dettinger et al. |
| 2016/0140828 A1 | 5/2016 | Deforest |
| 2016/0156584 A1 | 6/2016 | Hum et al. |
| 2016/0196635 A1 | 7/2016 | Cho et al. |
| 2016/0220225 A1 | 8/2016 | Wang et al. |
| 2016/0235374 A1 | 8/2016 | Miller et al. |
| 2016/0250517 A1 | 9/2016 | Tilvis et al. |
| 2016/0256741 A1 | 9/2016 | Holma et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0301794 A1 | 10/2016 | Schlakman et al. |
| 2016/0324457 A1 | 11/2016 | Dagum |
| 2016/0328736 A1 | 11/2016 | Wang et al. |
| 2016/0332025 A1 | 11/2016 | Repka |
| 2016/0346607 A1 | 12/2016 | Rapfogel |
| 2016/0375306 A1 | 12/2016 | Gu et al. |
| 2016/0379511 A1 | 12/2016 | Dawson et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0053542 A1 | 2/2017 | Wilson et al. |
| 2017/0095695 A1 | 4/2017 | Mangusson et al. |
| 2017/0153606 A1 | 6/2017 | Pitis et al. |
| 2017/0161014 A1 | 6/2017 | Kikugawa et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0319941 A1 | 11/2017 | Smith et al. |
| 2017/0330297 A1 | 11/2017 | Cronin et al. |
| 2017/0333752 A1* | 11/2017 | Korkala ............. A61B 5/02416 |
| 2017/0348562 A1 | 12/2017 | Jung et al. |
| 2017/0354845 A1 | 12/2017 | Williams et al. |
| 2017/0357520 A1 | 12/2017 | De vries et al. |
| 2018/0000426 A1 | 1/2018 | Li |
| 2018/0001184 A1 | 1/2018 | Tran et al. |
| 2018/0053200 A1 | 2/2018 | Cronin et al. |
| 2018/0056132 A1 | 3/2018 | Foley et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0126248 A1 | 5/2018 | Dion et al. |
| 2018/0189077 A1 | 7/2018 | Gupta et al. |
| 2018/0206766 A1 | 7/2018 | Blahnik et al. |
| 2018/0272190 A1 | 9/2018 | Miura et al. |
| 2018/0329584 A1 | 11/2018 | Williams et al. |
| 2018/0345078 A1 | 12/2018 | Blahnik et al. |
| 2019/0008467 A1 | 1/2019 | Averina et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0104951 A1 | 4/2019 | Valys et al. |
| 2019/0232110 A1 | 8/2019 | Williams et al. |
| 2019/0232111 A1 | 8/2019 | Williams et al. |

(56) References Cited

U.S. PATENT DOCUMENTS

| | | |
|---|---|---|
| 2019/0274565 A1 | 9/2019 | Soli et al. |
| 2019/0279520 A1 | 9/2019 | Wilson et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0387982 A1 | 12/2019 | Buller |
| 2020/0297249 A1 | 9/2020 | Williams et al. |
| 2020/0357522 A1 | 11/2020 | Pahwa et al. |
| 2020/0381100 A1 | 12/2020 | Williams et al. |
| 2020/0382613 A1 | 12/2020 | Sundstrom et al. |

FOREIGN PATENT DOCUMENTS

| | | |
|---|---|---|
| CN | 1397904 A | 2/2003 |
| CN | 1585943 A | 2/2005 |
| CN | 101150810 A | 3/2008 |
| CN | 101541387 A | 9/2009 |
| CN | 101651870 A | 2/2010 |
| CN | 101836894 A | 9/2010 |
| CN | 102339201 A | 2/2012 |
| CN | 102448555 A | 5/2012 |
| CN | 102804238 A | 11/2012 |
| CN | 102989159 A | 3/2013 |
| CN | 103212197 A | 7/2013 |
| CN | 103370924 A | 10/2013 |
| CN | 103403627 A | 11/2013 |
| CN | 104288983 A | 1/2015 |
| CN | 104501043 A | 4/2015 |
| CN | 106537397 A | 3/2017 |
| CN | 106709235 A | 5/2017 |
| CN | 106878550 A | 6/2017 |
| EP | 1935339 A1 | 6/2008 |
| EP | 2025368 A2 | 2/2009 |
| JP | 6-187118 A | 7/1994 |
| JP | 2001-76078 A | 3/2001 |
| JP | 2002-190007 A | 7/2002 |
| JP | 2003-337863 A | 11/2003 |
| JP | 2004-102609 A | 4/2004 |
| JP | 2005-79814 A | 3/2005 |
| JP | 2006-230679 A | 9/2006 |
| JP | 2007-260288 A | 10/2007 |
| JP | 2008-104758 A | 5/2008 |
| JP | 2008-183339 A | 8/2008 |
| JP | 2010-012335 A | 1/2010 |
| JP | 2010-122901 A | 6/2010 |
| JP | 2010-181280 A | 8/2010 |
| JP | 2011-125633 A | 6/2011 |
| JP | 2011-192126 A | 9/2011 |
| JP | 2011-198184 A | 10/2011 |
| JP | 2011-206323 A | 10/2011 |
| JP | 2011-259253 A | 12/2011 |
| JP | 2012-59264 A | 3/2012 |
| JP | 2012-524640 A | 10/2012 |
| JP | 2012-230503 A | 11/2012 |
| JP | 2013-103020 A | 5/2013 |
| JP | 2013-117690 A | 6/2013 |
| JP | 2013-544140 A | 12/2013 |
| JP | 2016-502875 A | 2/2016 |
| JP | 2016-177151 A | 10/2016 |
| JP | 2017-134689 A | 8/2017 |
| JP | 2017-532069 A | 11/2017 |
| KR | 10-2011-0017076 A | 2/2011 |
| KR | 10-2012-0023657 A | 3/2012 |
| KR | 10-2013-0111569 A | 10/2013 |
| KR | 10-2013-0111570 A | 10/2013 |
| KR | 10-2013-0135282 A | 12/2013 |
| KR | 10-2017-0003608 A | 1/2017 |
| WO | 1999/41682 A2 | 8/1999 |
| WO | 2002/27530 A2 | 4/2002 |
| WO | 2005/070289 A1 | 8/2005 |
| WO | 2010/126825 A1 | 11/2010 |
| WO | 2012/021507 A2 | 2/2012 |
| WO | 2012/061440 A2 | 5/2012 |
| WO | 2012/078079 A2 | 6/2012 |
| WO | 2013/052789 A1 | 4/2013 |
| WO | 2013/109762 A1 | 7/2013 |
| WO | 2013/109777 A1 | 7/2013 |
| WO | 2013/109916 A1 | 7/2013 |
| WO | 2013/173838 A2 | 11/2013 |
| WO | 2014/207294 A1 | 12/2014 |
| WO | 2015/198488 A1 | 12/2015 |
| WO | 2016/036582 A2 | 3/2016 |
| WO | 2017/037242 A1 | 3/2017 |

OTHER PUBLICATIONS

Summons to Attend Oral Proceedings received for European Patent Application No. 18154145.9, mailed on Sep. 17, 2020, 11 pages.
Corrected Notice of Allowance received for U.S. Appl. No. 14/732,773, dated Mar. 24, 2020, 3 pages.
Non-Final Office Action received for U.S. Appl. No. 15/925,652, dated Aug. 7, 2020, 39 pages.
Office Action received for Australian Patent Application No. 2019250251, dated Aug. 6, 2020, 3 pages.
Summons to Attend Oral Proceedings received for European Patent Application No. 17810749.6, mailed on Aug. 12, 2020, 11 pages.
Advisory Action received for U.S. Appl. No. 16/144,864, dated Jul. 6, 2020, 6 pages.
Applicant-Initiated Interview Summary received for U.S. Appl. No. 15/705,849, dated Jun. 29, 2020, 3 pages.
Office Action Received for Danish Patent Application No. PA201670656, dated Jul. 1, 2020, 4 pages.
Office Action received for Japanese Patent Application No. 2019-044107, dated May 29, 2020, 6 pages (3 pages of English Translation and 3 pages of Official Copy).
Notice of Allowance received for Chinese Patent Application No. 201580037927.5, dated Oct. 17, 2019, 3 pages (1 page of English Translation and 2 pages of Official Copy).
Office Action received for Australian Patent Application No. 2019222943, dated Oct. 3, 2019, 3 pages.
Office Action received for Danish Patent Application No. PA201770191, dated Oct. 25, 2019, 4 pages.
Applicant Initiated Interview Summary received for U.S. Appl. No. 15/627,069, dated Nov. 4, 2019, 6 pages.
Applicant Initiated Interview Summary received for U.S. Appl. No. 15/600,243, dated Nov. 1, 2019, 6 pages.
Applicant Initiated Interview Summary received for U.S. Appl. No. 15/608,848, dated Nov. 1, 2019, 3 pages.
Non-Final Office Action received for U.S. Appl. No. 15/705,849, dated Nov. 12, 2019, 15 pages.
Final Office Action received for U.S. Appl. No. 15/608,848, dated Aug. 21, 2020, 15 pages.
Final Office Action received for U.S. Appl. No. 16/138,809, dated Aug. 27, 2020, 24 pages.
Office Action received for Australian Patent Application No. 2017277971, dated Aug. 12, 2020, 3 pages.
Office Action received for Chinese Patent Application No. 201380081349.6, dated Jul. 15, 2020, 9 pages (4 pages of English Translation and 5 pages of Official Copy).
Office Action received for Korean Patent Application No. 10-2019-7025538, dated Aug. 15, 2020, 8 pages (4 pages of English Translation and 4 pages of Official Copy).
Applicant-Initiated Interview Summary received for U.S. Appl. No. 15/627,069, dated Jul. 20, 2020, 5 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Notice of Allowance received for U.S. Appl. No. 16/144,735, dated Jul. 21, 2020, 13 pages.
Office Action received for Australian Patent Application No. 2018268972, dated Jul. 9, 2020, 4 pages.
Applicant-Initiated Interview Summary received for U.S. Appl. No. 15/705,849, dated Feb. 14, 2020, 3 pages.
Corrected Notice of Allowance received for U.S. Appl. No. 14/732,773, dated Feb. 10, 2020, 3 pages.
Corrected Notice of Allowance received for U.S. Appl. No. 15/600,243, dated Feb. 5, 2020, 3 pages.

(56) References Cited

OTHER PUBLICATIONS

Non-Final Office Action received for U.S. Appl. No. 15/608,848, dated Feb. 6, 2020, 12 pages.
Non-Final Office Action received for U.S. Appl. No. 16/144,735, dated Feb. 19, 2020, 10 pages.
Notice of Allowance received for U.S. Appl. No. 16/144,671, dated Feb. 10, 2020, 17 pages.
Office Action received for Chinese Patent Application No. 201380081349.6, dated Jan. 16, 2020, 11 pages (6 pages of English Translation and 5 pages of Official Copy).
Office Action received for Japanese Patent Application No. 2018-014096, dated Jan. 6, 2020, 17 pages (8 pages of English Translation and 9 pages of Official Copy).
Office Action received for Chinese Patent Application No. 201810105846.X, dated Nov. 28, 2019, 9 pages (5 pages of English Translation and 4 pages of Official Copy).
Office Action received for Danish Patent Application No. PA201870378, dated Jan. 6, 2020, 3 pages.
Office Action received for European Patent Application No. 16837432.0, dated Jan. 10, 2020, 7 pages.
Office Action received for European Patent Application No. 19721883.7, dated Jan. 10, 2020, 4 pages.
Applicant-Initiated Interview Summary received for U.S. Appl. No. 16/138,809, dated Jun. 9, 2020, 7 pages.
Final Office Action received for U.S. Appl. No. 16/144,864, dated May 28, 2020, 29 pages.
Non-Final Office Action received for U.S. Appl. No. 15/627,069, dated May 26, 2020, 25 pages.
Non-Final Office Action received for U.S. Appl. No. 16/378,136, dated Jun. 2, 2020, 8 pages.
Office Action received for European Patent Application No. 19721883.7, dated May 28, 2020, 11 pages.
Applicant Initiated Interview Summary received for U.S. Appl. No. 15/608,848, dated May 12, 2020, 5 pages.
Final Office Action received for U.S. Appl. No. 15/705,849, dated May 1, 2020, 17 pages.
Final Office Action received for U.S. Appl. No. 16/144,735, dated May 4, 2020, 12 pages.
Non-Final Office Action received for U.S. Appl. No. 16/377,892, dated May 21, 2020, 9 pages.
Notice of Acceptance received for Australian Patent Application No. 2019222943, dated May 5, 2020, 3 pages.
Corrected Notice of Allowance received for U.S. Appl. No. 15/600,243, dated Mar. 31, 2020, 5 pages.
Office Action received for Australian Patent Application No. 2019100495, dated Mar. 16, 2020, 3 pages.
Supplemental Notice of Allowance received for U.S. Appl. No. 16/144,849, dated Mar. 31, 2020, 2 pages.
"Fitbit App", Available online at: <http://web.archive.org/web/20180114083150/https://www.fitbit.com/au/app>, Jan. 14, 2018, 8 pages.
Non-Final Office Action received for U.S. Appl. No. 16/144,849, dated Sep. 17, 2019, 3 pages.
Office Action received for Australian Patent Application No. 2019100495, dated Sep. 17, 2019, 7 pages.
Office Action received for Chinese Patent Application No. 201810105846.X, dated Aug. 27, 2019, 12 pages (5 pages of English Translation and 7 pages of Official Copy).
Applicant-Initiated Interview Summary received for U.S. Appl. No. 16/144,735, dated Jun. 18, 2020, 3 pages.
Applicant-Initiated Interview Summary received for U.S. Appl. No. 16/144,753, dated Jun. 18, 2020, 3 pages.
Applicant-Initiated Interview Summary received for U.S. Appl. No. 16/144,864, dated Jun. 22, 2020, 3 pages.
Office Action received for Australian Patent Application No. 2017277971, dated Jun. 3, 2020, 3 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,864, dated Jul. 28, 2020, 27 pages.
Office Action received for Chinese Patent Application No. 201680047983.1, dated Jul. 1, 2020, 6 pages (3 pages of English Translation and 3 pages of Official Copy).
Corrected Notice of Allowance received for U.S. Appl. No. 15/600,243, dated Mar. 13, 2020, 3 pages.
Final Office Action received for U.S. Appl. No. 15/627,069, dated Mar. 2, 2020, 22 pages.
Non-Final Office Action received for U.S. Appl. No. 16/144,753, dated Mar. 5, 2020, 9 pages.
Non-Final Office Action received for U.S. Appl. No. 16/138,809, dated Feb. 28, 2020, 22 pages.
Notice of Allowance received for Chinese Patent Application No. 201810105846.X, dated Feb. 18, 2020, 2 pages (1 page of English Translation and 1 page of Official Copy).
Notice of Allowance received for U.S. Appl. No. 16/144,849, dated Mar. 6, 2020, 9 pages.
Office Action received for Australian Patent Application No. 2019100495, dated Mar. 6, 2020, 3 pages.
Office Action received for Danish Patent Application No. PA201870380, dated Mar. 5, 2020, 2 pages.
Office Action received for Japanese Patent Application No. 2019-162293, dated Jan. 31, 2020, 8 pages (4 pages of English Translation and 4 pages of Official Copy).
Office Action received for Korean Patent Application No. 10-2019-7025538, dated Feb. 17, 2020, 12 pages (6 pages of English Translation and 6 pages of Official Copy).
Wesley, "Apple Watch Series 1" online available at: - http://toolbox.info/blog/archives/1737-unknown.html, May 28, 2015, 5 pages (Official copy only) (See Communication under 37 CFR § 1.98(a)(3)).
Youtube, "Apple Watch Series 3", Online available at:—https://www.youtube.com/watch?v=iBPr9gEfkK8, Nov. 21, 2017, 15 pages (Official copy only) (See Communication under 37 CFR § 1.98(a)(3)).
Advisory Action received for U.S. Appl. No. 16/144,864, dated Jul. 29, 2019, 6 pages.
Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/839,922, dated Mar. 24, 2017, 4 pages.
Advisory Action received for U.S. Appl. No. 16/144,849, dated Aug. 12, 2019, 5 pages.
Certificate of Examination received for Australian Patent Application No. 2018101855, dated Aug. 6, 2019, 2 pages.
Certification of Examination received for Australian Patent Application No. 2018100158, dated Oct. 23, 2018, 2 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Decision to Grant received for Danish Patent Application No. PA201870379, dated Jul. 5, 2019, 2 pages.
Decision to Refuse received for European Application No. 13811085.3, dated Sep. 11, 2018, 21 pages.
Decision to Refuse received for European Patent Application No. 15771747.1, dated Aug. 10, 2018, 22 pages.
"DwProgressBar v2: Stepping and Events", davidwalsh.name/dwprogressbar-2-stepping-events-mootools-progress-bar, retrieved from the Wayback Machine, Aug. 31, 2008, 4 pages.
Extended European Search Report received for European Patent Application No. 16837432.0, dated Mar. 11, 2019, 10 pages.
Extended European Search Report received for European Patent Application No. 18154145.9, dated Mar. 2, 2018, 8 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/839,922, dated Dec. 14, 2016, 22 pages.

(56) References Cited

OTHER PUBLICATIONS

Final Office Action received for U.S. Appl. No. 15/608,848, dated Jun. 26, 2019, 27 pages.
Final Office Action received for U.S. Appl. No. 15/925,652, dated Aug. 1, 2019, 30 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
"Graphs and Charts", Online available at: https://www.teachervision.com/lesson-planning/graph-chart-teacher-resources, retrieved on Dec. 12, 2018, 4 pages.
Intention to Grant received for Danish Patent Application No. PA201570668, dated Mar. 27, 2017, 2 pages.
Intention to Grant received for Danish Patent Application No. PA201870379, dated May 2, 2019, 2 pages.
International Preliminary Report on Patentability received for PCT Application No. PCT/US2016/037686, dated Mar. 1, 2018, 12 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/047282, dated Mar. 16, 2017, 26 pages.
International Preliminary Report on Patentability received for PCT Patent Application No. PCT/US2017/035554, dated Dec. 20, 2018, 39 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/024570, dated Aug. 8, 2019, 18 pages.
International Written Opinion received for PCT Patent Application No. PCT/US2013/073195, dated Jun. 23, 2014, 8 pages.
Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No. PCT/US2017/035554, dated Jul. 20, 2017, 2 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
"Mugs", Online Available at: https://web.archive.org/web/20151029034349/http://le-mugs.com/, Oct. 29, 2015.
"Multi-Set Bar Chart", The Data Visualization Catalogue, Available Online at: https://datavizcatalogue.com/methods/multiset_barchart.html, Feb. 8, 2014, 3 pages.
"My CalStep", http://www.surprisesoftware.com/mycalstep/, retrieved from the Wayback Machine, May 9, 2007, 2 pages.
Non-Final Office Action Received for U.S. Appl. No. 16/144,864, dated Dec. 18, 2018, 19 pages.
Non-Final Office Action received for U.S. Appl. No. 15/608,848, dated Nov. 2, 2018, 21 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018, 45 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 15/183,663, dated Jul. 9, 2018, 13 pages.
Non-Final Office Action received for U.S. Appl. No. 15/600,243, dated Jun. 27, 2019, 17 pages.
Non-Final Office Action received for U.S. Appl. No. 15/627,069, dated Jun. 21, 2019, 22 pages.
Non-Final Office Action received for U.S. Appl. No. 15/925,652, dated Apr. 5, 2019, 28 pages.
Non-Final Office Action received for U.S. Appl. No. 16/144,849, dated Dec. 31, 2018, 28 pages.
Notice of Acceptance received for Australian Patent Application No. 2015312215, dated Oct. 9, 2017, 3 pages.
Notice of Acceptance received for Australian Patent Application No. 2019201583, dated Jul. 15, 2019, 3 pages.
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages (1 page of English Translation and 3 pages of Official Copy).
Notice of Allowance received for Japanese Patent Application No. 2016-557650, dated Apr. 9, 2019, 4 pages (1 page of English Translation and 3 pages of Official Copy).
Notice of Allowance received for Korean Patent Application No. 10-2016-7014577, dated May 30, 2019, 5 pages (2 pages of English Translation and 3 pages of Official Copy).
Notice of Allowance received for Korean Patent Application No. 10-2016-7033638, dated May 31, 2017, 5 pages (2 pages of English Translation and 3 pages of Official Copy).
Notice of Allowance received for Taiwanese Patent Application No. 104128685, dated May 3, 2017, 3 pages (Official Copy Only) {See Communication under 37 CFR § 1.98(a) (3)}.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 15/183,663, dated Jan. 17, 2019, 6 pages.
Notice of Allowance received for U.S. Appl. No. 15/616,480, dated Jan. 3, 2019, 8 pages.
Office Action received for Australian Patent Application No. 2015312215, dated Oct. 13, 2016, 3 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Chinese Patent Application No. 201380081349.6, dated Feb. 26, 2019, 12 pages (6 pages of English Translation and 6 pages of Official Copy).
Office Action received for Chinese Patent Application No. 201380081349.6, dated Jul. 15, 2019, 10 pages (5 pages of English Translation and 5 pages Of Official copy).
Office Action received for Chinese Patent Application No. 201580037927.5, dated Apr. 22, 2019, 9 pages (4 pages of English Translation and 5 pages of Official Copy).

(56) References Cited

OTHER PUBLICATIONS

Office Action received for Chinese Patent Application No. 201580037927.5, dated Jul. 20, 2018, 21 pages (6 pages of English Translation and 15 pages of Official copy).
Office Action received for Chinese Patent Application No. 201680047983.1, dated Mar. 18, 2019, 18 pages (6 pages of English Translation and 12 pages of Official Copy).
Office Action received for Chinese Patent Application No. 201810105846,X, dated Feb. 25, 2019, 10 pages (5 pages of English Translation and 5 pages of Official copy).
Office Action Received for Danish Patent Application No. PA201670656, dated Nov. 3, 2016, 8 pages.
Office Action received for Danish Patent Application No. PA201570666, dated Jun. 27, 2016, 4 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated May 2, 2019, 4 pages.
Office Action Received for Danish Patent Application No. PA201670656, dated May 30. 2018, 5 pages.
Office Action received for Danish Patent Application No. PA201770191, dated Jan. 25, 2018. 3 pages.
Office Action received for Danish Patent Application No. PA201770191 dated Nov. 21, 2018, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870379, dated Feb. 28, 2019, 3 pages.
Office Action eceived for Danish Patent Application No. PA201870380, dated Mar. 27, 2019, 4 pages.
Office Action received for Danish Patent Application No. PA201870380, dated Sep. 11, 2018, 9 pages.
Office Action received for European Patent Application No. 13811085.3, dated Apr. 20, 2018, 15 pages.
Office Action received for European Patent Application No. 17810749.6, dated Aug. 20, 2019, 9 pages.
Office Action received for European Patent Application No. 18154145.9, dated Apr. 3, 2018, 6 pages.
Office Action received for European Patent Application No. 15771747.1, dated Oct. 31, 2017, 7 pages.
Office Action received for German Patent Application No. 112015002326.7, dated Feb. 20, 2019, 7 pages (2 pages of English Translation and 5 pages of Official Copy).
Office Action received for Japanese Patent Application No. 2016-535045, dated May 12, 2017, 10 pages (5 pages of English Translation and 5 pages of Official Copy).
Office Action received for Japanese Patent Application No. 2016-557650, dated Apr. 13, 2018, 9 pages (5 pages of English Translation and 4 pages of Official Copy).
Office Action received for Japanese Patent Application No. 2016-557650, dated Aug. 10, 2017, 10 pages (5 pages of English Translation and 5 pages of Official Copy).
Office Action received for Japanese Patent Application No. 2016-557650, dated Nov. 9, 2018, 6 pages (3 pages of English Translation and 3 pages of Official copy).
Office Action received for Japanese Patent Application No. 2018-014096, dated Jun. 29, 2018, 20 pages (11 pages of English Translation and 9 pages of Official Copy).
Office Action received for Japanese Patent Application No. 2018-014096, dated May 8, 2019, 14 pages (7 pages of English Translation and 7 pages of Official Copy).
Office Action received for Japanese Patent Application No. 2018-014096, dated Nov. 6, 2018, 15 pages (7 pages of English Translation and 8 pages of Official Copy).
Office Action received for Japanese Patent Application No. 2018-068846, dated Jan. 8, 2019, 6 pages (3 pages of English Translation and 3 pages of Official copy).
Office Action received for Korean Patent Application No. 10-2016-7014577, dated Dec. 26, 2017, 14 pages (6 pages of English Translation and 8 pages of Official Copy).
Office Action received for Korean Patent Application No. 10-2016-7014577, dated Oct. 31, 2018, 11 pages (5 pages of English Translation and 6 pages of Official Copy).
Office Action received for Korean Patent Application No. 10-2016-7033638, dated Jan. 31, 2017, 6 pages (2 pages of English Translation and 4 pages of Official Copy).
Office Action received for Taiwanese Patent Application No. 104128685, dated Jan. 4, 2017, 40 pages (15 pages of English Translation and 25 pages of Official Copy).
Partial Supplementary European Search Report received for European Patent Application No. 17810749.6, dated Apr. 25, 2019, 8 pages.
Search report and opinion received for Danish Patent Application No. PA201770191, dated Jun. 30, 2017, 9 pages.
Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870379 dated Sep. 14, 2018, 9 pages.
Summons to attend oral proceedings received for European Patent Application No. 13811085.3, mailed on Jan. 26, 2018, 14 pages.
Summons to Attend Oral Proceedings received for European Patent Application No. 15771747.1, dated May 25, 2018, 17 pages.
Supplemental Notice of Allowance received for U.S. Appl. No. 15/616,480, dated Mar. 28, 2019, 2 pages.
Supplementary European Search Report received for European Patent Application No. 17810749.6, dated Aug. 6, 2019, 6 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
"Utilization of Galaxy S4—S Health, ChatOn and Samsung Hub", Available at: http://seeit.kr/1263, Jun. 12, 2013, 25 pages (Official Copy only) {See Communication under 37 CFR § 1.98(a) (3)}.
"Visual Pace Alarm app", Available Online at: https://apps.garmin.com/en-US/apps/3940f3a2-4847-4078-a911-d77422966c82, Oct. 19, 2016, 1 page.
Final Office Action received for U.S. Appl. No. 12/205,847, dated Apr. 25, 2012, 42 pages.
Non-Final Office Action received for U.S. Appl. No. 12/205,847, dated Oct. 3, 2011, 59 pages.
Notice of Allowance received for U.S. Appl. No. 12/205,847, dated Aug. 20, 2012, 13 pages.
Non-Final Office Action received for U.S. Appl. No. 14/839,916, dated Feb. 4, 2016, 19 pages.
Non-Final Office Action received for U.S. Appl. No. 14/839,922, dated Feb. 25, 2016, 20 pages.
Apple, "iPhone User's Guide", Available at: http://mesnotices.20minutes.fr/manuel-notice-mode-ernploi/APPLE/IPHONE%2D%5FE#, Retrieved on Mar. 27, 2008, Jun. 2007, 137 pages.
Cho, H. S, "Satisfactory Innovative Smart-watch (fitbit force) . . . review after seven days of use, such as the amount of sleep and movement (improving sleep is the object of X-Blue", Online Available at: https://x-blueuv.blogspot.com/2013/12/fitbit-force.html, Dec. 3, 2013, 6 pages (Official Copy Only) {See Communication under 37 Cfr § 1.98(a) (3)}.
CNET, "Google Fit's automatic activity tracking is getting smarter on Android Wear", Available online at: https://www.youtube.com/watch?v=IttzICid_d8, May 18, 2016, 1 page.
Codrington, Simon, "Intuitive Scrolling Interfaces with CSS Scroll Snap Points", Online Available at: https://www.sitepoint.com/intuitive-scrolling-interfaces-with-css-scroll-snap-points!, Dec. 8, 2015, 14 pages.
Evergreen, et al, "Bar Chart", Better Evaluation, Available Online at: https://www.betterevaluation.org/en/evaluation-options/BarChart, Oct. 31, 2014, 8 pages.

(56) References Cited

OTHER PUBLICATIONS

Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.
Jenbsjourney, "Wondering About a Fitbit?", Available at: https://jenbsjourney.blogspot.kr/2013/08/wondering-about-fitbit.html, Aug. 6, 2013, 12 pages.
Office Action received for Danish Patent Application No. PA201570666, dated Feb. 2, 2016, 9 pages.
Office Action received for Danish Patent Application No. PA201570668, dated Apr. 8, 2016, 8 pages.
International Search Report received for PCT Patent Application No. PCT/US2013/073195, dated Jun. 23, 2014, 3 pages.
Invitation to Pay Additional Fees received for PCT Patent Application No. PCT/US2015/047282, dated Dec. 22, 2015, 7 pages.
Rainmaker, "Garmin Fenix3 New Auto Climb Functionality", Available online at: https://www.youtube.com/watch?v=iuavOSNpVRc, Feb. 19, 2015, 1 page.
Razykdreviews, "In Depth Review of Apple Watch Activity and Workout App", available at: https://www.youtube.com/watch?v=GkKI3qIK0ow, May 11, 2015, 1 page.
Rizknows, "Garmin Connect Mobile App—Review #2", https://www.youtube.com/watch?v=7my3wMpeRbE, Oct. 22, 2015, 1 page.
Rizknows, "Tom Tom Multisport Cardio Review", Online available at: https://www.youtube.com/watch?v=WoVCzLrSN9A, Sep. 4, 2015, 1 page.
Smith, "Garmin Fenix 5 Activity/Smart Watch Review", Online Available at: https://www.youtube.com/watch?v=6PkQxXQxpoU, Sep. 2, 2017, 1 page.
Sportstechguides, "Garmin Fenix 5: How to Add Power Data Fields", Online Available at: https://www.youtube.com/watch?v=ZkPptnnXEiQ, Apr. 29, 2017, 2 pages.
Sportstechguides, "Garmin Fenix 5: How to Set Up Run Alerts", Online Available at: https://www.youtube.com/watch?v=gSMwv8vIhB4, May 13, 2017, 2 pages
Suunto, "Suunto Spartan—Heart Rate Zones", Online Available at: https://www.youtube.com/watch?v=aixfoCnS0OU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TOMTOM, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Zlelik, "Garmin Fenix 5 Open Water Swimming Activity Demo", Online Available at: https://www.youtube.com/watch?v=iSVhdvw2dcs, Jun. 9, 2017, 1 page.
Applicant Initiated Interview Summary received for U.S. Appl. No. 16/144,864, dated Apr. 29, 2020, 4 pages.
Non-Final Office Action received for U.S. Appl. No. 16/418,786, dated Apr. 24, 2020, 16 pages.
Notice of Allowance received for U.S. Appl. No. 16/144,849, dated Apr. 17, 2020, 2 pages.
Office Action received for Chinese Patent Application No. 201710439448.7, dated Mar. 27, 2020, 13 pages (7 pages of English Translation and 6 pages of Official Copy).
International Search Report and written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.

Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Office Action received for Japanese Patent Application No. 2019-162293, dated Jul. 27, 2020, 9 pages (5 pages of English Translation and 4 pages of Official Copy).
Result of Consultation received for European Patent Application No. 18154145.9, dated Sep. 4, 2020, 3 pages.
Search Report and Opinion received for Danish Patent Application No. PA201970532, dated Nov. 8, 2019, 9 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
International Preliminary Report on Patentability received for PCT Patent Application No. PCT/US2018/031662, dated Nov. 28, 2019, 12 pages.
Notice of Allowance received for Japanese Patent Application No. 2018-068846, dated Dec. 9, 2019, 4 pages (1 page of English Translation and 3 pages of Official Copy).
Notice of Allowance received for U.S. Appl. No. 14/732,773, dated Dec. 18, 2019, 21 pages.
Notice of Allowance received for U.S. Appl. No. 15/600,243, dated Dec. 12, 2019, 7 pages.
Office Action received for Chinese Patent Application No. 201680047983.1, dated Nov. 28, 2019, 9 pages (4 pages of English Translation and 5 pages of Official Copy).
Office Action received for Korean Patent Application No. 10-2019-7025781, dated Nov. 26, 2019, 10 pages (4 pages of English Translation and 6 pages of Official Copy).
Applicant Initiated Interview Summary received for U.S. Appl. No. 16/144,849, dated Jan. 21, 2020, 6 pages.
Non-Final Office Action received for U.S. Appl. No. 16/144,864, dated Jan. 31, 2020, 29 pages.
Applicant Initiated Interview Summary received for U.S. Appl. No. 15/608,848, dated Oct. 26, 2020, 3 pages.
Applicant-Initiated Interview Summary received for U.S. Appl. No. 15/925,652, dated Nov. 3, 2020, 4 pages.
Applicant-Initiated Interview Summary received for U.S. Appl. No. 16/138,809, dated Dec. 16, 2020, 7 pages.
Applicant-Initiated Interview Summary received for U.S. Appl. No. 16/144,753, dated Nov. 4, 2020, 3 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
Bagala et al., "Evaluation of Accelerometer-Based Fall Detection Algorithms on Real World Falls", PloS One, vol. 7, Issue 5, May 16, 2012, 9 pages.
Board Decision received for Chinese Patent Application No. 201380081349.6, dated Nov. 23, 2020, 2 pages (1 page of English Translation and 1 page of Official Copy).
European Search Report received for European Patent Application No. 20182116.2, dated Oct. 21, 2020, 4 pages.
Final Office Action received for U.S. Appl. No. 15/627,069, dated Oct. 20, 2020, 25 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/035199, dated Oct. 30, 2020, 20 pages.

(56) References Cited

OTHER PUBLICATIONS

Invitation to Pay Additional Fees received for PCT Patent Application No. PCT/US2020/035199, dated Sep. 8, 2020, 12 pages.
Non-Final Office Action received for U.S. Appl. No. 16/820,383, dated Dec. 14, 2020, 11 pages.
Non-Final Office Action received for U.S. Appl. No. 16/894,309, dated Oct. 15, 2020, 24 pages.
Non-Final Office Action received for U.S. Appl. No. 17/031,859, dated Dec. 15, 2020, 13 pages.
Notice of Allowance received for U.S. Appl. No. 15/705,849, dated Oct. 16, 2020, 14 pages.
Notice of Allowance received for U.S. Appl. No. 15/925,652, dated Nov. 20, 2020, 9 pages.
Notice of Allowance received for U.S. Appl. No. 16/144,735, dated Oct. 28, 2020, 13 pages.
Notice of Allowance received for U.S. Appl. No. 16/144,753, dated Dec. 4, 2020, 22 pages.
Notice of Allowance received for U.S. Appl. No. 16/144,864, dated Sep. 29, 2020, 2 pages.
Office Action received for Chinese Patent Application No. 201710439448.7, dated Oct. 10, 2020, 19 pages (8 pages of English Translation and 11 pages of Official Copy).
Office Action received for European Patent Application No. 20182116.2, dated Nov. 6, 2020, 9 pages.
Office Action received for Japanese Patent Application No. 2020-104679, dated Sep. 18, 2020, 13 pages (7 pages of English Translation and 6 pages of Official Copy).
Office Action received for Korean Patent Application No. 10-2019-7025781, dated Oct. 30, 2020, 10 pages (4 pages of English Translation and 6 pages of Official Copy).
Result of Consultation received for European Patent Application No. 17810749.6, dated Dec. 15, 2020, 3 pages.
Result of Consultation received for European Patent Application No. 18154145.9, dated Nov. 30, 2020, 17 pages.
Result of Consultation received for European Patent Application No. 19721883.7, dated Oct. 7, 2020, 3 pages.
Non-Final Office Action received for U.S. Appl. No. 17/031,874, dated Dec. 28, 2020, 14 pages.

* cited by examiner

800 ─┐

806
In response to measuring the activity-based value of the swim characteristic and in accordance with notification criteria being met, issue, via the one or more perceptual output mechanisms, a perceptual notification that has a first perceptual property based on the measured activity-based value of the swim characteristic.

818
In accordance with the measured activity-based value of the swim characteristic having a first measured value, the first perceptual property has a first perceptual value.

820
The first perceptual value is a first color that corresponds to the first measured value of the swim characteristic.

822
The first perceptual value is a first number of taps that corresponds to the first measured value of the swim characteristic.

806
In response to measuring the activity-based value of the swim characteristic and in accordance with notification criteria being met, issue, via the one or more perceptual output mechanisms, a perceptual notification that has a first perceptual property based on the measured activity-based value of the swim characteristic.

824
In accordance with the measured activity-based value of the swim characteristic having a second measured value, different than the first measured value, the first perceptual property has a second perceptual value, different than the first perceptual value > 826
> The second perceptual value is a second color that corresponds to the second measured value of the swim characteristic.

> 828
> The second perceptual value is a second number of taps that corresponds to the second measured value of the swim characteristic.

*FIG. 8C*

SWIM TRACKING AND NOTIFICATIONS FOR WEARABLE DEVICES

CROSS-REFERENCE TO RELATED APPLICATIONS

This application claims priority to U.S. Provisional App Ser. No. 62/739,133, entitled "SWIM TRACKING AND NOTIFICATIONS FOR WEARABLE DEVICES", filed on Sep. 28, 2018, the content of which is hereby incorporated by reference in its entirety.

FIELD

The present disclosure relates generally to computer user interfaces, and more specifically to techniques for providing activity-based notifications.

BACKGROUND

Swimmers who are swimming frequently use wearable devices to monitor activity-based metrics related to swimming characteristics. For example, swimmers want to monitor their pace, swim time, and a swim direction for open swimming. Notifications are often difficult for swimmers to read while swimming because they contain too much text. Providing perceptual notifications that are optimized to convey information in a glance allow swimmers to obtain information about the measured activity-based metrics in real-time during their swim without having to stop.

BRIEF SUMMARY

Notifications including large amounts of text are generally cumbersome and difficult for a swimmer to read while swimming. For example, notifications displaying blocks of information, such as a pace, elapsed time, swim distance, and calories burned, are difficult for swimmers to read at a glance and while in motion. Existing notifications require a swimmer to pause or stop to read the notification, interrupting swimmers' swim workouts. In some instances, swimmers must interact with the notification in order to see the information in the notification, which is not only disruptive for the swimmer, but also drains battery. This latter consideration is particularly important in battery-operated devices.

Accordingly, the present technique provides electronic devices with faster, more efficient methods and interfaces for providing swimmers with notifications while swimmers are swimming. Such methods and interfaces optionally complement or replace other methods for providing perceptual notifications that can convey measured activity-based values efficiently. Such methods and interfaces reduce the cognitive burden on a swimmer and produce a more efficient human-machine interface. For battery-operated computing devices, such methods and interfaces conserve power and increase the time between battery charges. Such techniques also allow swimmers to more efficiently obtain swimming-related notifications from electronic devices in environments where the swimmer is unable to stop to read text.

In accordance with some embodiments, a method is provided. The method is performed at an electronic device with one or more perceptual output mechanisms and one or more sensors. The method comprises: measuring, via the one or more sensors, an activity-based value of a swim characteristic; in response to measuring the activity-based value of the swim characteristic. In accordance with notification criteria being met, issuing, via the one or more perceptual output mechanisms, a perceptual notification that has a first perceptual property based on the measured activity-based value of the swim characteristic. In accordance with the measured activity-based value of the swim characteristic having a first measured value, the first perceptual property has a first perceptual value. In accordance with the measured activity-based value of the swim characteristic having a second measured value, different than the first measured value, the first perceptual property has a second perceptual value, different than the first perceptual value.

In accordance with some embodiments, a non-transitory computer-readable storage medium is provided. The medium stores one or more programs configured to be executed by one or more processors of an electronic device with one or more perceptual output mechanisms and one or more sensors. The one or more programs including instructions for: measuring, via the one or more sensors, an activity-based value of a swim characteristic; in response to measuring the activity-based value of the swim characteristic. In accordance with notification criteria being met, issuing, via the one or more perceptual output mechanisms, a perceptual notification that has a first perceptual property based on the measured activity-based value of the swim characteristic. In accordance with the measured activity-based value of the swim characteristic having a first measured value, the first perceptual property has a first perceptual value. In accordance with the measured activity-based value of the swim characteristic having a second measured value, different than the first measured value, the first perceptual property has a second perceptual value, different than the first perceptual value.

In accordance with some embodiments, a transitory computer-readable storage medium is provided. The medium stores one or more programs configured to be executed by one or more processors of an electronic device with one or more perceptual output mechanisms and one or more sensors. The one or more programs including instructions for: measuring, via the one or more sensors, an activity-based value of a swim characteristic; in response to measuring the activity-based value of the swim characteristic. In accordance with notification criteria being met, issuing, via the one or more perceptual output mechanisms, a perceptual notification that has a first perceptual property based on the measured activity-based value of the swim characteristic. In accordance with the measured activity-based value of the swim characteristic having a first measured value, the first perceptual property has a first perceptual value. In accordance with the measured activity-based value of the swim characteristic having a second measured value, different than the first measured value, the first perceptual property has a second perceptual value, different than the first perceptual value.

In accordance with some embodiments, an electronic device is provided. The electronic device comprises: one or more perceptual output mechanisms, one or more sensors, one or more processors; and memory storing one or more programs configured to be executed by the one or more processors, the one or more programs including instructions for: measuring, via the one or more sensors, an activity-based value of a swim characteristic; in response to measuring the activity-based value of the swim characteristic. In accordance with notification criteria being met, issuing, via the one or more perceptual output mechanisms, a perceptual notification that has a first perceptual property based on the measured activity-based value of the swim characteristic. In accordance with the measured activity-based value of the swim characteristic having a first measured value, the first perceptual property has a first perceptual value. In accordance with the measured activity-based value of the swim characteristic having a second measured value, different than the first measured value, the first perceptual property has a second perceptual value, different than the first perceptual value.

In accordance with some embodiments, an electronic device with one or more perceptual output mechanisms and one or more sensors is provided. The electronic device comprises: means for measuring, via the one or more sensors, an activity-based value of a swim characteristic; in response to measuring the activity-based value of the swim characteristic. In accordance with notification criteria being met, the electronic device comprises means for issuing, via the one or more perceptual output mechanisms, a perceptual notification that has a first perceptual property based on the measured activity-based value of the swim characteristic. In accordance with the measured activity-based value of the swim characteristic having a first measured value, the first perceptual property has a first perceptual value. In accordance with the measured activity-based value of the swim characteristic having a second measured value, different than the first measured value, the first perceptual property has a second perceptual value, different than the first perceptual value.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for providing notifications, thereby increasing the effectiveness, efficiency, and user satisfaction with such devices. Such methods and interfaces may complement or replace other methods for providing notifications that provide swimming metrics while a swimmer is swimming.

DESCRIPTION OF THE FIGURE S

For a better understanding of the various described embodiments, reference should be made to the Description of Embodiments below, in conjunction with the following drawings in which like reference numerals refer to corresponding parts throughout the figures.

FIGS. 8A-8C are flow diagrams illustrating a method for providing perceptual notifications based on measured activity-based values.

DESCRIPTION OF EMBODIMENTS

Figure 1A:
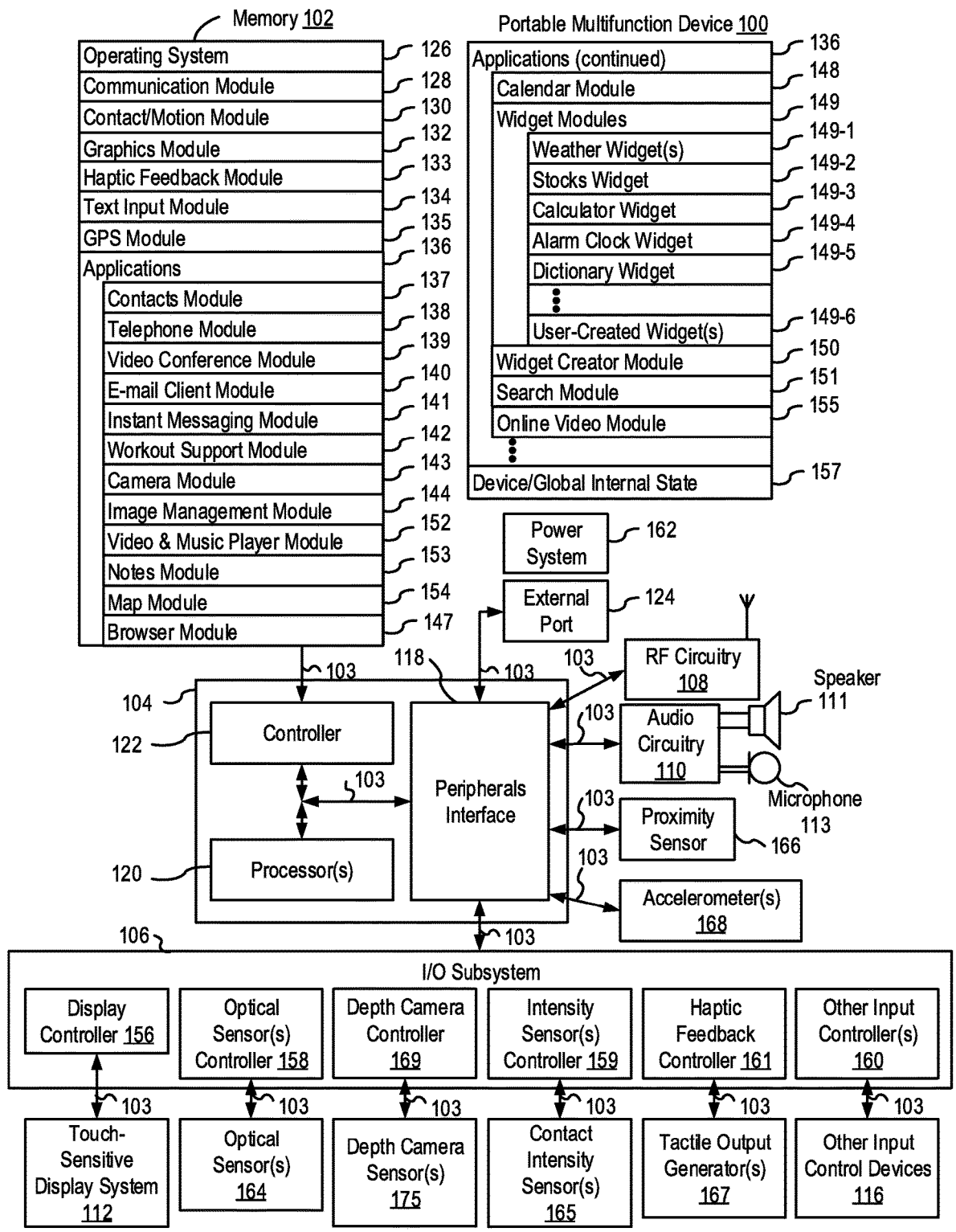
FIG. 1A is a block diagram illustrating a portable multifunction device with a touch-sensitive display in accordance with some embodiments.

The following description sets forth exemplary methods, parameters, and the like. It should be recognized, however, that such description is not intended as a limitation on the scope of the present disclosure but is instead provided as a description of exemplary embodiments.

There is a need for electronic devices that provide perceptual notifications that are optimized to convey information in a glance to allow swimmers to obtain swim metrics without having to stop. Such techniques can reduce the cognitive burden on a swimmer who relies on notifications for performance or navigation during an open swim, thereby enhancing productivity. Further, such techniques can reduce processor and battery power otherwise wasted on redundant user inputs.

Below, FIGS. 1A-1B, 2, 3, 4A-4B, and 5A-5B provide a description of exemplary devices for performing the techniques for managing event notifications. FIGS. 6A-6J illustrate exemplary user interfaces for providing perceptual notifications based on measured values while a swimmer is swimming. FIGS. 7A-7D illustrate exemplary user interfaces for providing perceptual notifications that provide directions for a swimmer while the swimmer is swimming in the ocean. FIGS. 8A-8C are flow diagrams illustrating methods for providing perceptual notifications, in accordance with some embodiments. The user interfaces in FIGS. 6A-6J and FIGS. 7A-7D are used to illustrate the processes described below, including the processes in FIGS. 8A-8C.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300) These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1.4 are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RE circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LEI) (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture settles with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
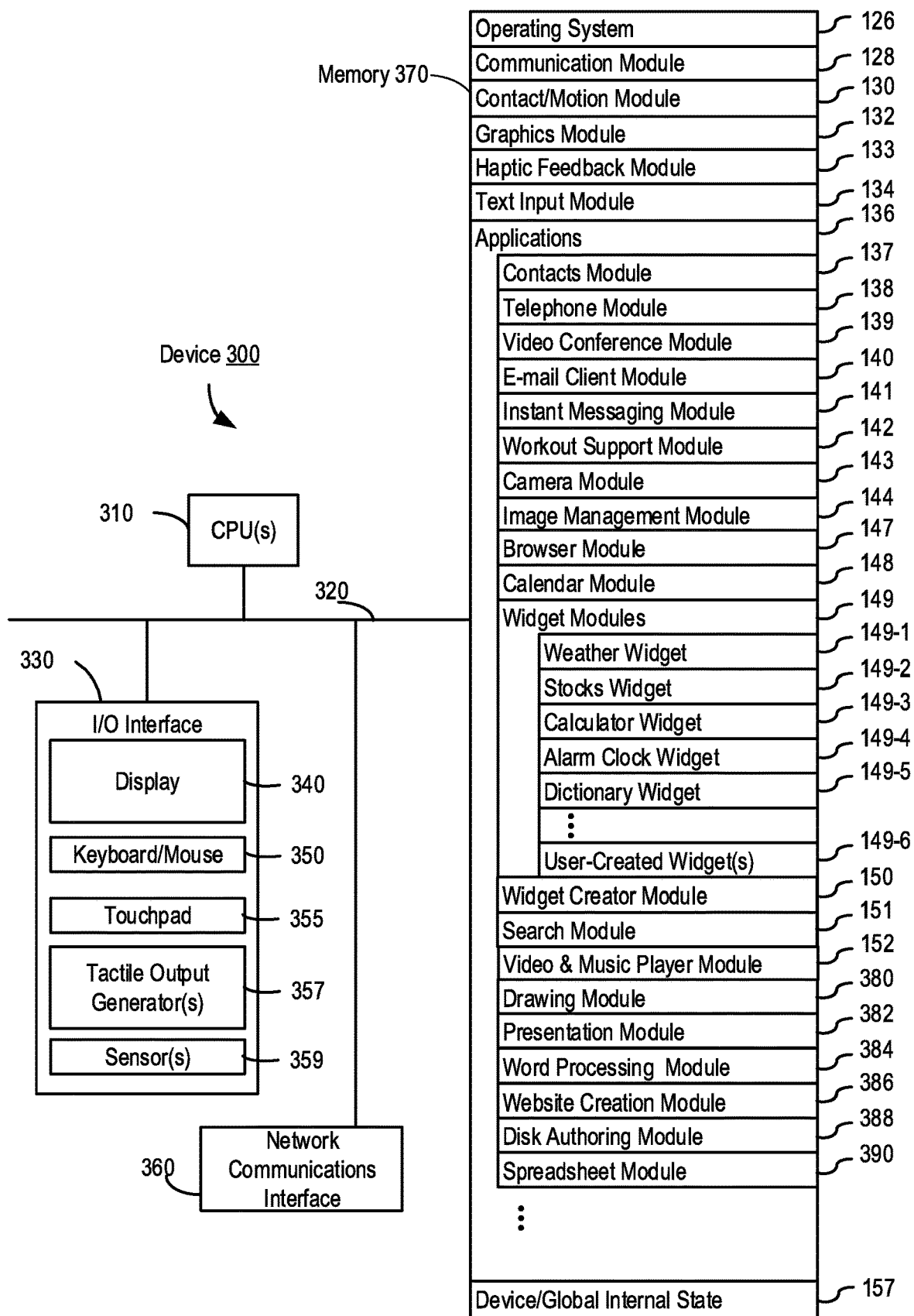
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multi-touch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or 141; and so forth.

In conjunction with RE circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RE circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RE circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript tile. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
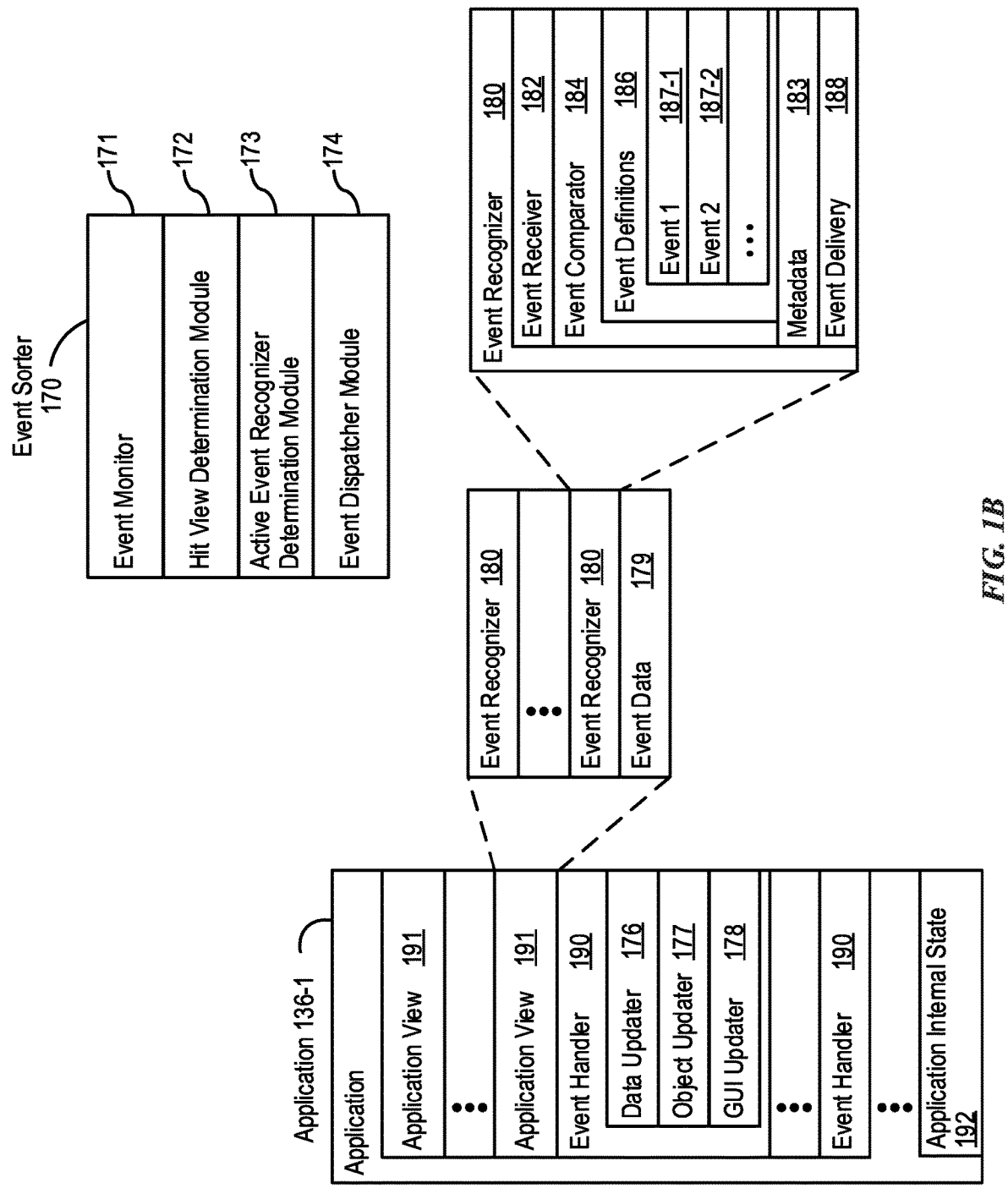
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
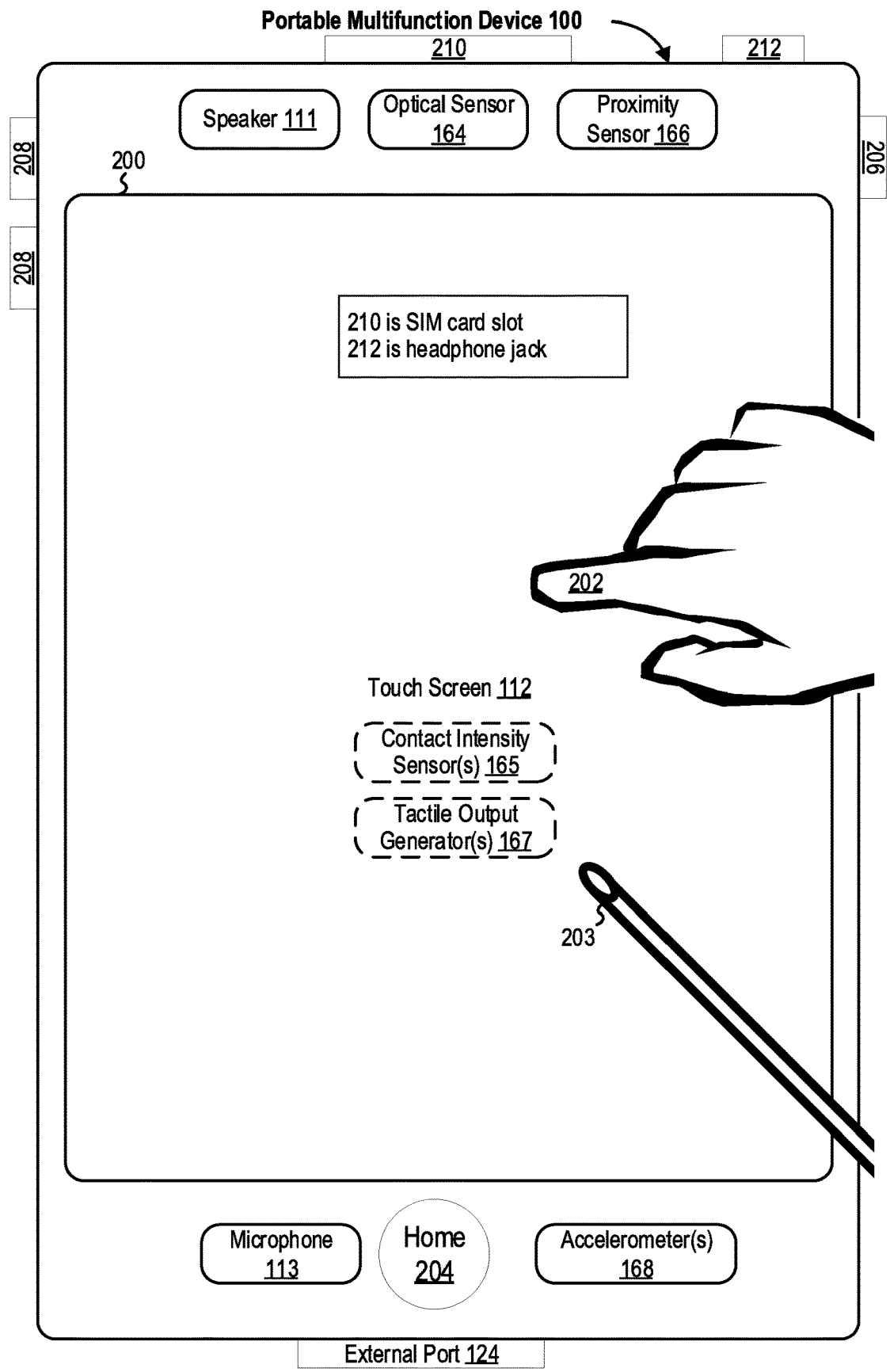
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are optionally, implemented on, for example, portable multifunction device 100.

Figure 4A:
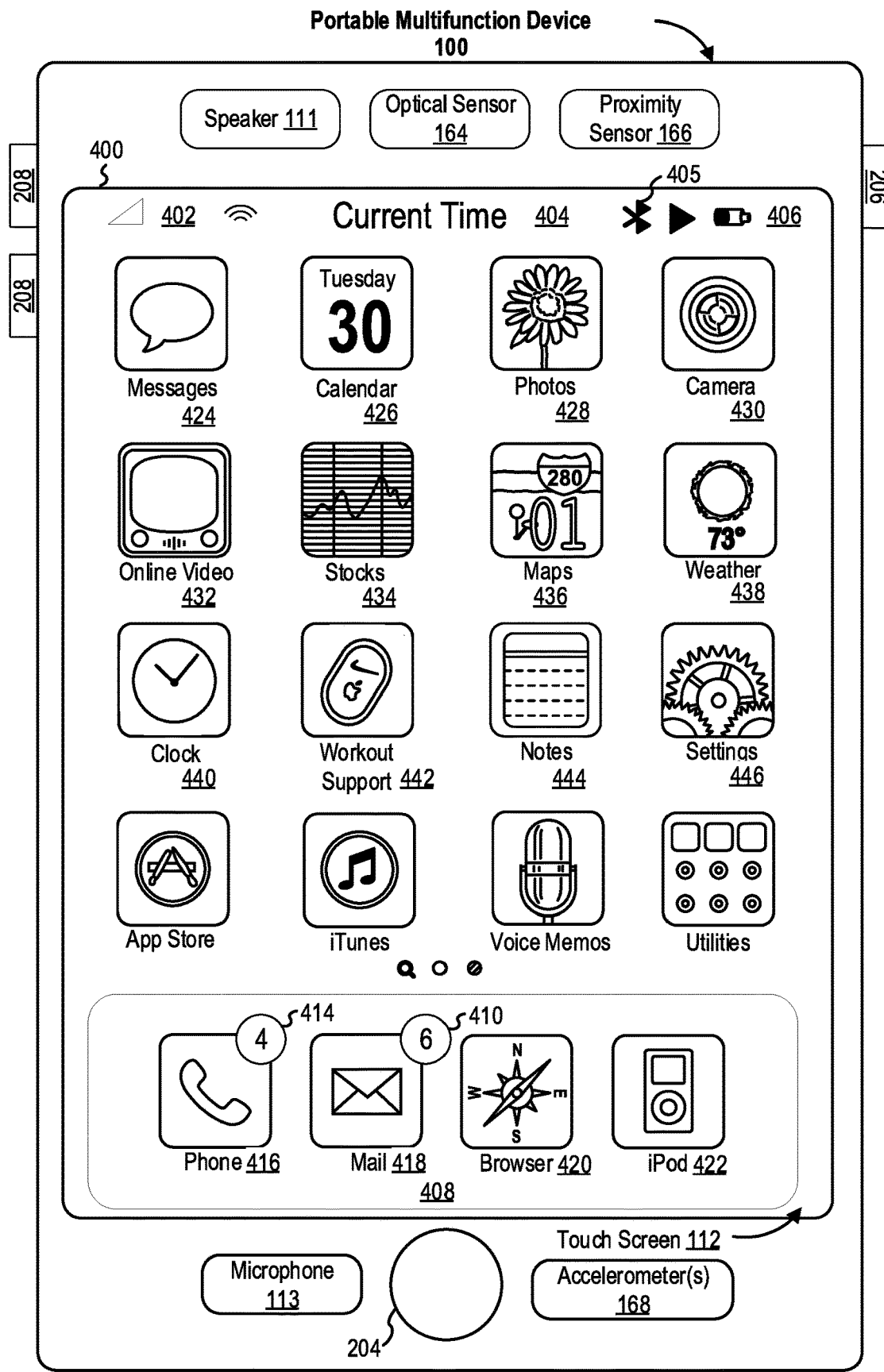
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar,"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks,"
  Icon 436 for map module 154, labeled "Maps,"
  icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
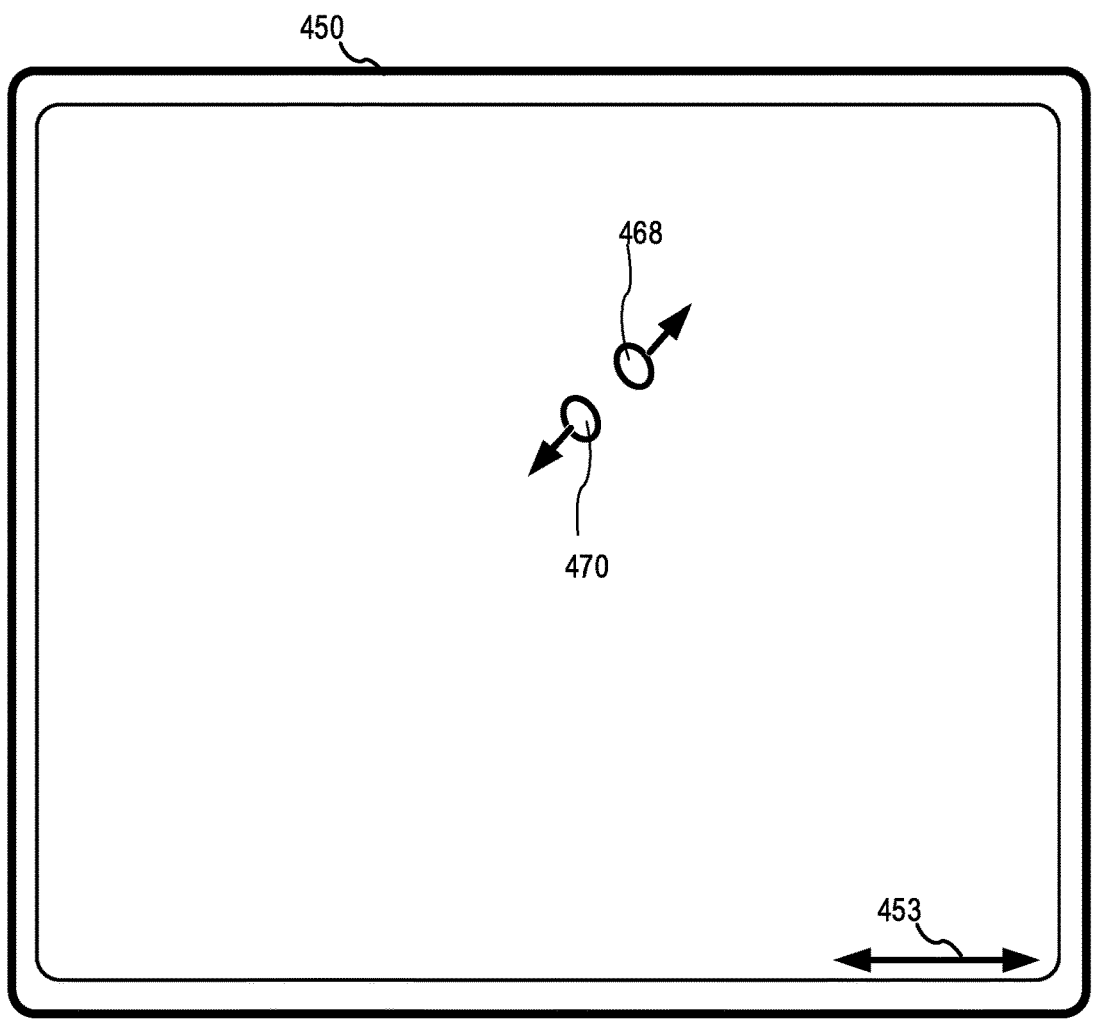
FIG. 4B illustrates an exemplary user interface for a multifunction device with a touch-sensitive surface that is separate from the display in accordance with some embodiments.
Figure 4B:
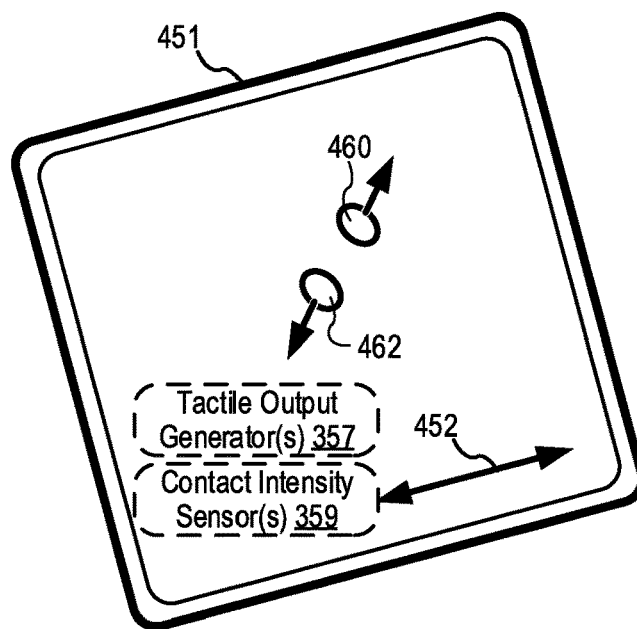

FIG. 4B illustrates an exemplary user interface on a device (e.g., device 300, FIG. 3 with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 413) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
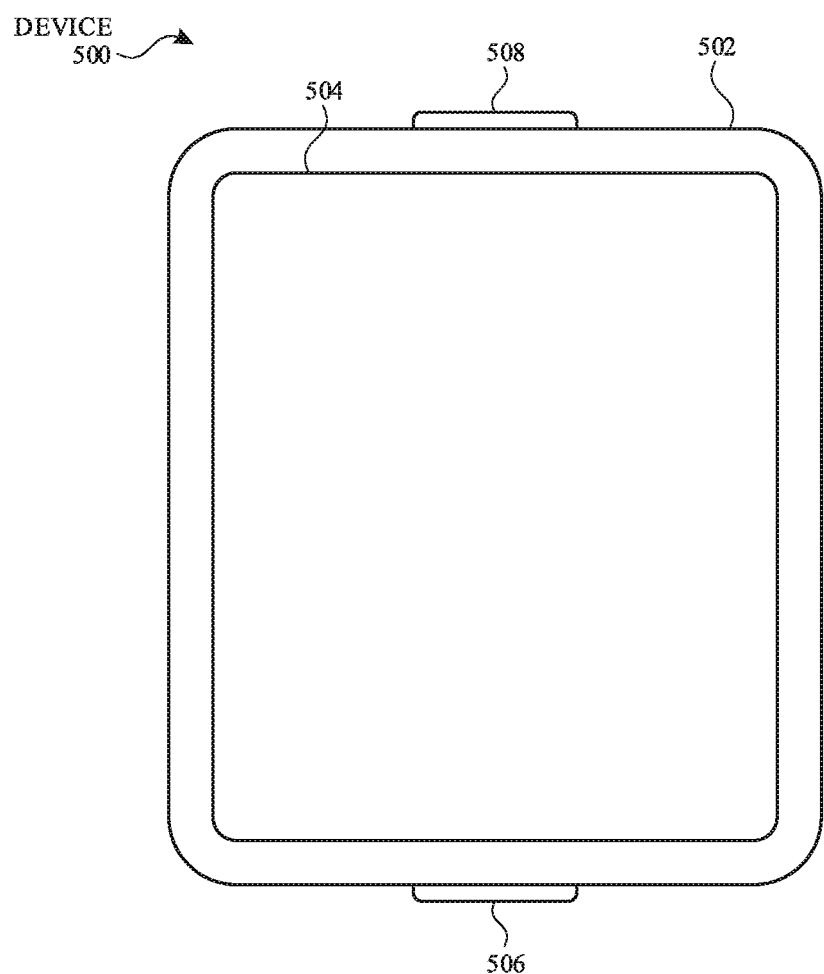
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
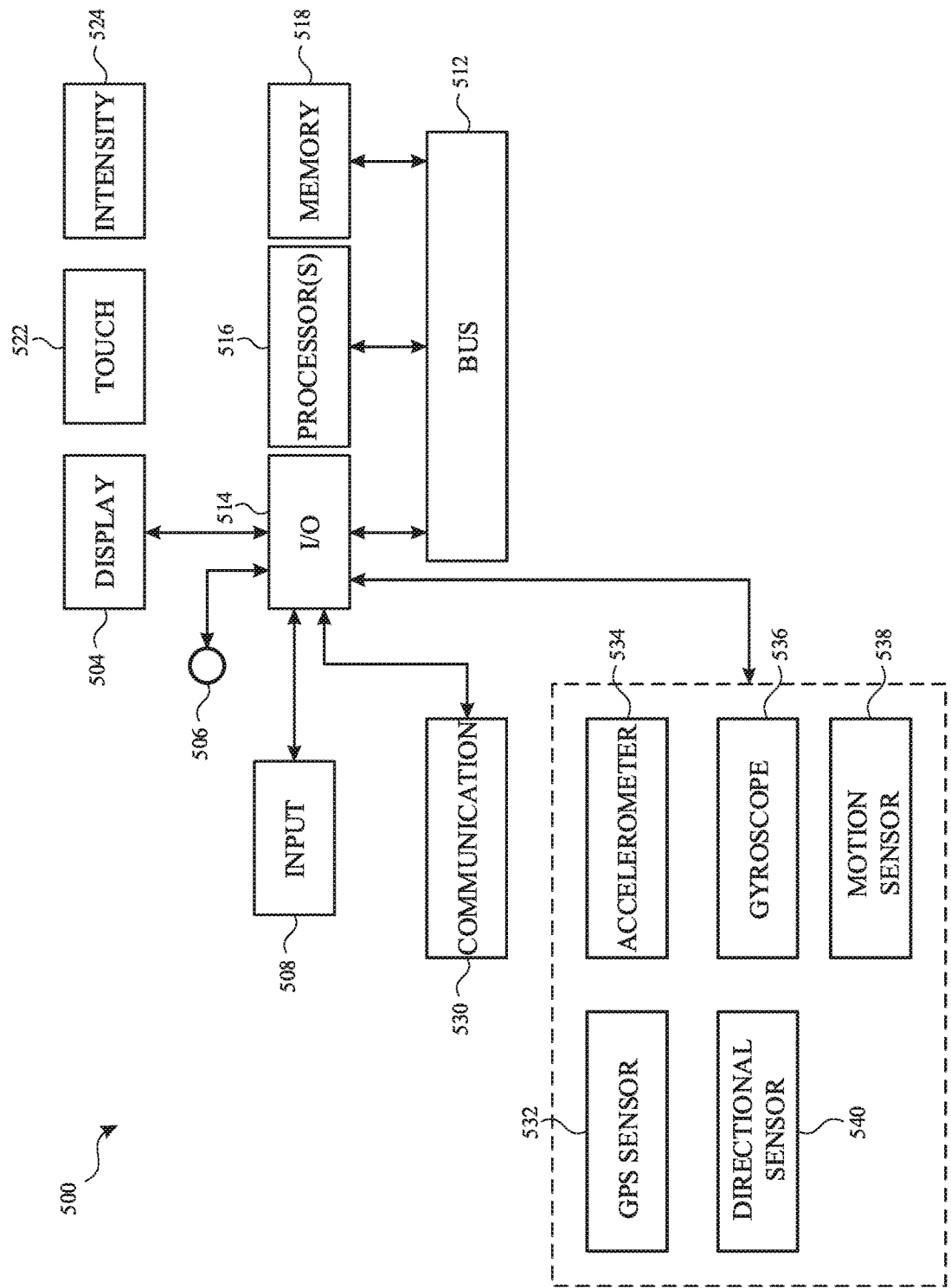
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to 110 section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 800 (FIGS. 8A-8C). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6J and FIGS. 7A-7D illustrate exemplary user interfaces for providing perceptual notifications based on activity-based values of a swim characteristic while a swimmer is swimming, in accordance with some embodiments. The user interfaces in these figures are used to illustrate the processes described below, including the processes in FIGS. 8A-8C.

Figure 6A:
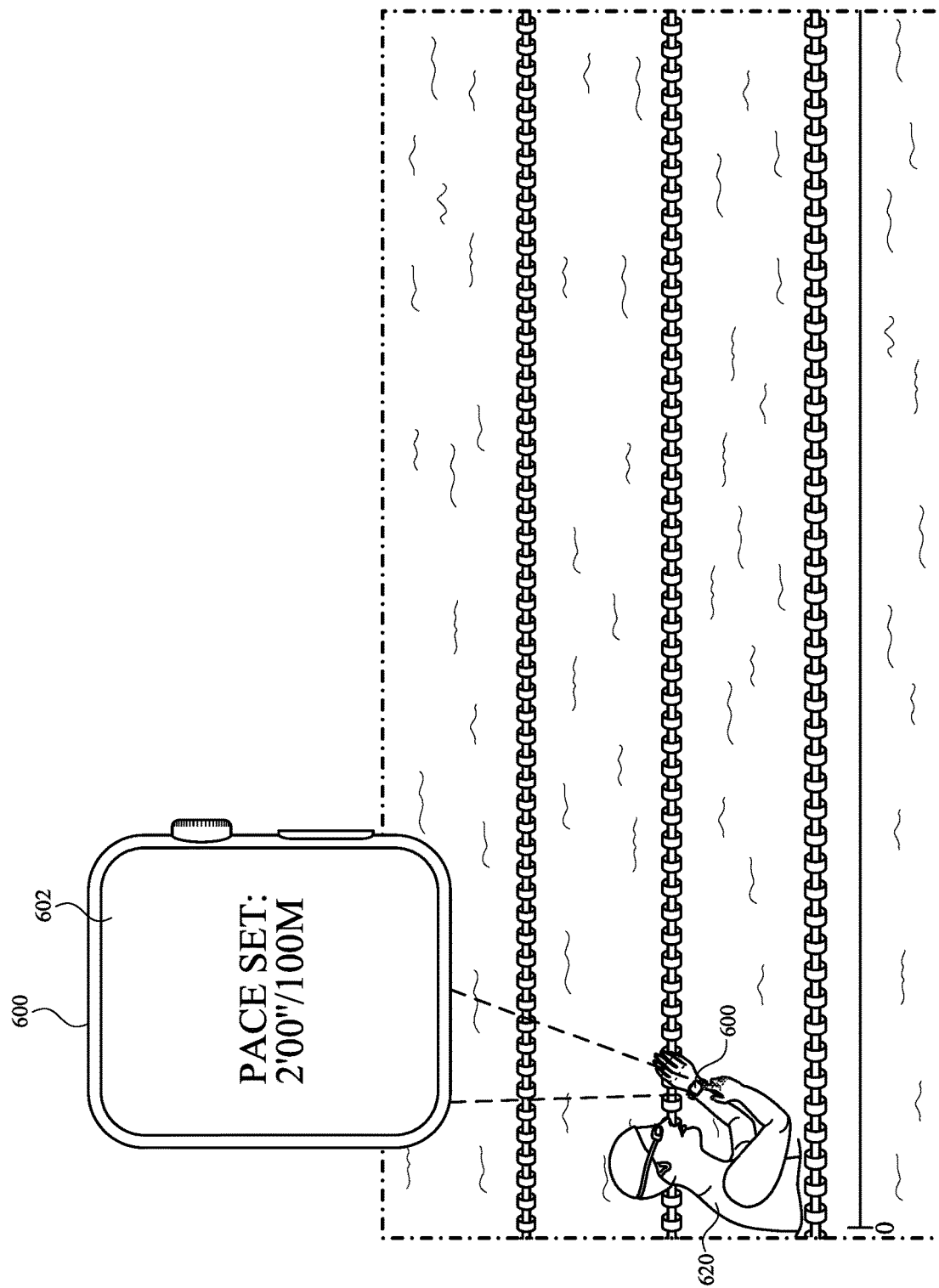
FIGS. 6A-6J illustrate exemplary techniques for providing perceptual notifications using measured activity-based values.

FIGS. 6A-6J illustrate device 600, worn by swimmer 620. In some embodiments, device 600 includes one or more features of device 100, 300, or 500. Device 600 includes display 602, at least one haptic output generator, at least one activity sensor (e.g., an accelerometer) and at least one orientation sensor. As seen in FIG. 6A, swimmer 620 is preparing to engage in a physical activity, specifically a lap swim, while wearing device 600.

As discussed in more detail below, as swimmer 620 is swimming, device 600 measures swim characteristics such as pace, distance, laps, direction, time, and/or number of calories burned during the swimmer's swim. Device 600 issues one or more perceptual notifications (e.g., visual notifications 624A, 626A, haptic notifications 628A) that are based on the measured value of one or more of the swim characteristics (e.g., a pace as swimmer 620 is swimming.

In FIG. 6A, device 600 displays, on display 602, a set target pace of swimmer 620 as 2'00"/100 m (2 minutes and 0 seconds per 100 meters). In some embodiments, the set target pace was set at device 600 (e.g., via a pace setting user interface of device 600). In some embodiments, the set target pace is received from an external electronic device. As shown in FIG. 6A, device 600 does not provide any initial perceptual notifications because swimmer 620 has not yet started swimming.

Figure 6B:
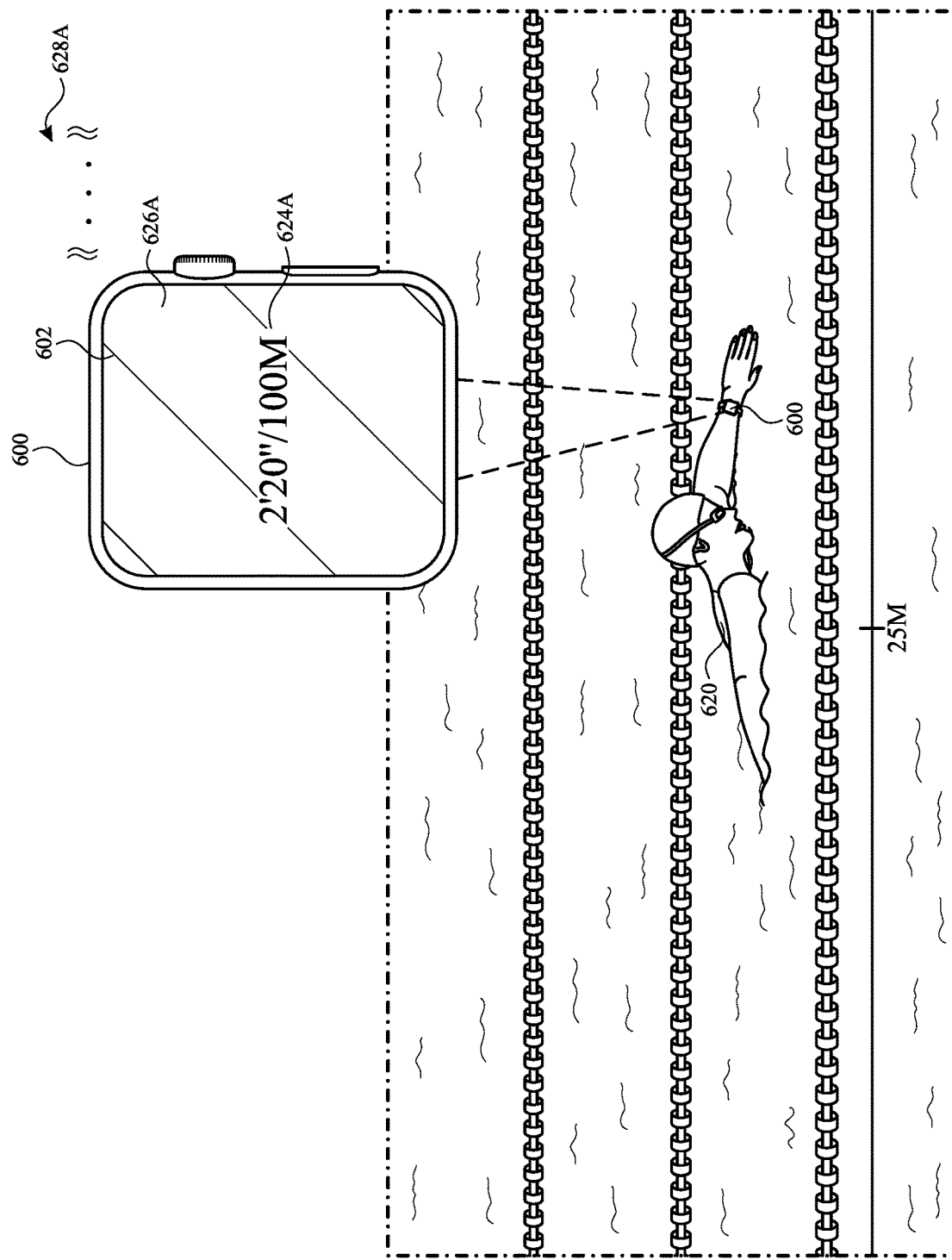

In FIG. 6B, device 600 is currently executing an activity tracking function, including measuring (e.g., via a GPS sensor, using stroke detection, an accelerometer, or a gyroscope) swimmer 620's pace, a swim characteristic. Device 600 is also displaying visual notification 626A, which includes text that reflects swimmer 620's current pace of 2'20"/100 m. In some embodiments, the text of visual notification 626A includes additional measured values of additional swim characteristics, such as the elapsed swim time, distance, strokes, etc. The text of visual notification 624A is displayed in a large font that spans display 602 so that swimmer 620 can easily discern the swim pace from a quick glance.

Device 600 also displays visual notification 626A, which is a display of a substantially uniform red color (as denoted by the left-to-right diagonal hatching of notification 626A) across display 602. Device 600 illuminates the displayed color (e.g., a perceptual characteristic of the notification) at an increased brightness to make it easier for swimmer 620 to see the notification while swimming. Device 600 selects a red color to display in visual notification 626A based on the current swim pace of swimmer 620 being below the target pace set by swimmer 620, as illustrated in FIG. 6A. Device 600 displays a visual notification 624A and/or 626A when device 600 determines that notification criteria are met. In the embodiment of FIG. 6A, the notification criteria includes a viewable criterion. A viewable criterion is satisfied when device 600 determines that a physical condition is met, such as detecting swimmer's 600 arm position being moved to a position where display 602 of device 600 is in front of swimmer 620. As illustrated in FIG. 6A, device 600 detects that swimmer's left arm is positioned in front of swimmer 620 during a freestyle stroke. In response to determining the swimmer's left arm satisfies the viewable criterion, device 600 issues a visual notification 624A, 626A that includes visual information about the pace of swimmer 620 by displaying the measured pace and a substantially uniform display of a red color. Device 600 issues notifications when the viewable criterion, in particular, is satisfied in order to conserve power and only provide visual notifications when swimmer can actually see it, which results in a more efficient user-device interface.

Notification criteria also includes a time criterion and a distance criterion. A time criterion is satisfied when device 600 determines that swimmer 620 has been swimming for at least a threshold period of time, or for at least a threshold period of time since the previous notification. For example, device 600 obtains a 5 second notification time period from swimmer 620, prior to swimmer 620 beginning the swim workout. Thus, when device 600 determines that at least 5 seconds has passed since the last notification (and device 600 determines that other notification criterion in notification criteria), device 600 issues visual alerts 624A, 626A. Similarly, a distance criterion is satisfied when device 600 determines that swimmer 620 has swain a at least a threshold distance or at least a threshold distance since the last notification. For example, device 600 obtains a setting to issue a notification every 25 meters. Thus, when device 600 determines that swimmer 620 has swam at least 25 m since the last notification (and device 600 determines that other notification criterion in notification criteria), device 600 issues a visual alert 624A, 626A.

Device 600 also issues haptic notification 628A, which includes two haptic taps separated by a long pause (e.g., a lower frequency). Device 600 outputs the haptic taps at a lower frequency to indicate that the measured pace is below the set target pace. Device 600 optionally varies the number of haptic taps, frequency of the tap, and intensity (e.g., perceptual characteristics of the notification) of the tap to indicate whether the measured pace is above or below the target pace. Device 600 outputs a haptic notification 628A when notification criteria are satisfied, such as when the viewable criterion, time criterion, and distance criterion are met as discussed above. In some embodiments, a haptic notification 628A (but not a visual notification) is issued even when the viewable criterion is not met because the haptic output does not require a swimmer to view display 602 of device 600 to obtain information from the haptic notification 628A.

Figure 6C:
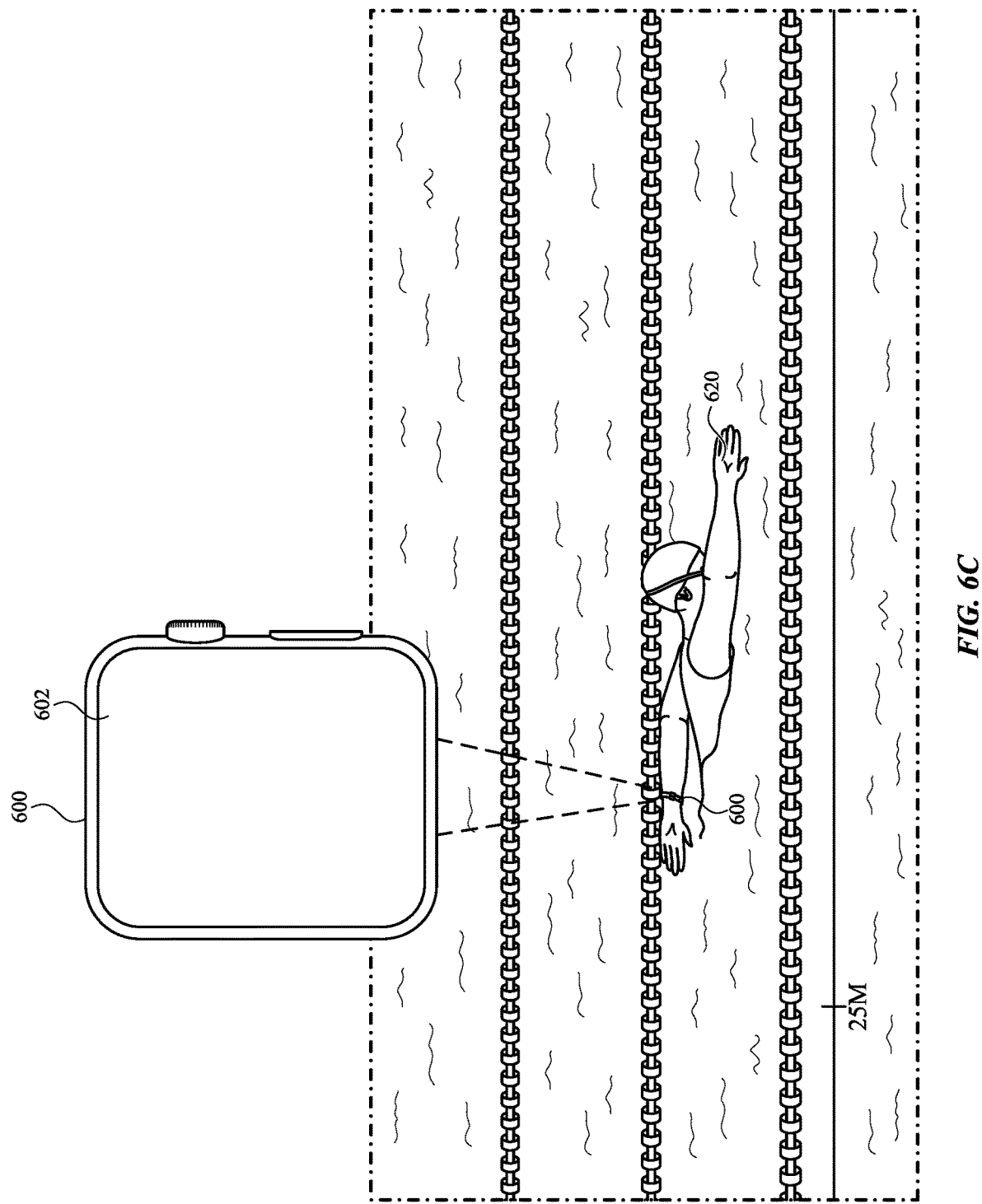

At FIG. 6C, device 600 forgoes displaying a visual because the notification criteria is not satisfied. In particular, the viewable criterion is not satisfied because device 600 determines that the swimmer 620's left arm (e.g., the arm wearing the watch) is behind swimmer 620. Therefore, swimmer 620 would not be able to see display 602. When the viewable criterion is not satisfied, device 600 forgoes issuing a visual notification. Device 600 optionally turns of display 602 when no visual notification is displayed to conserve battery. Device 600 optionally forgoes issuing a haptic notification when the viewable criterion is not met.

Figure 6D:
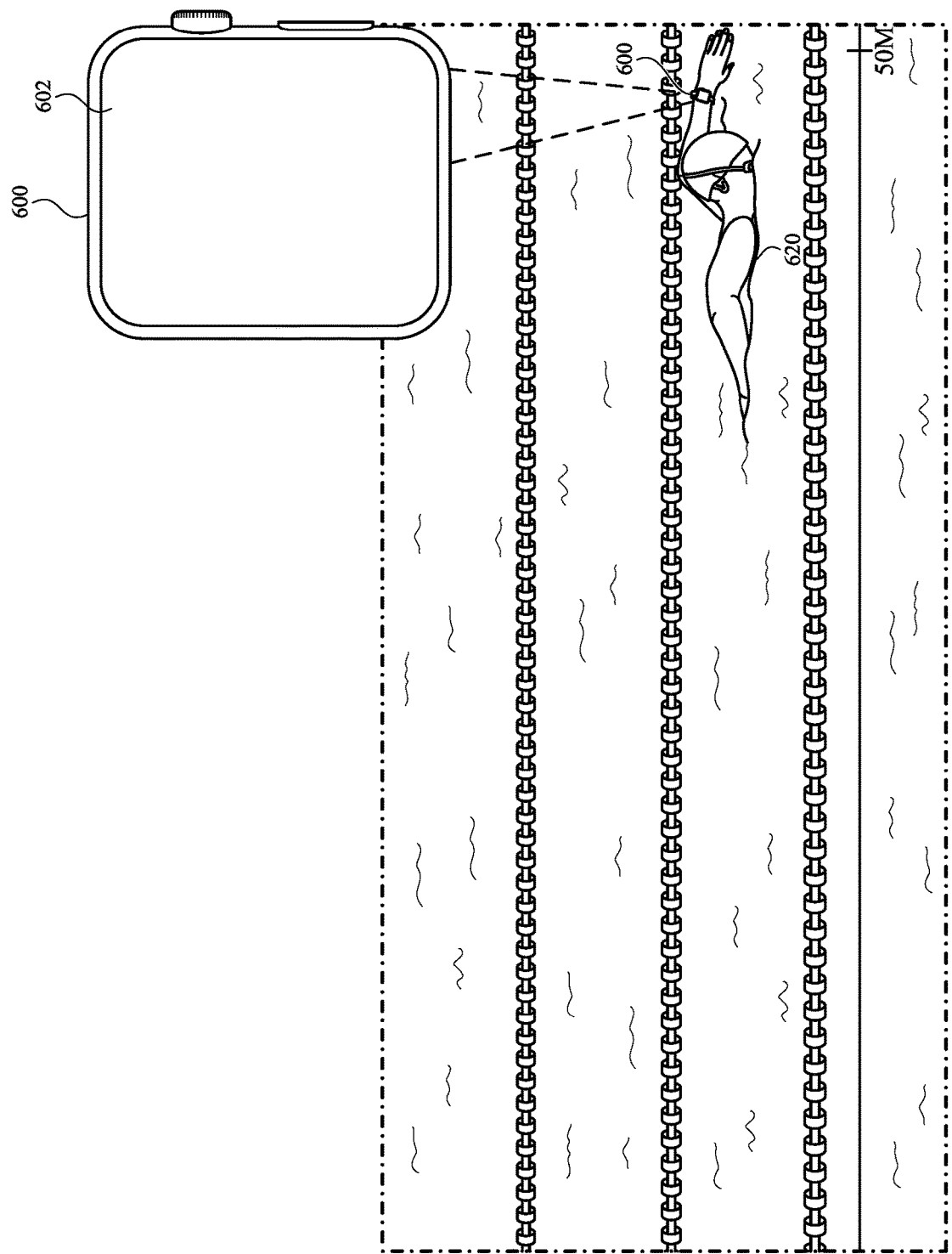

At FIG. 6D, device 600 forgoes displaying a visual notification because notification criteria are not satisfied when a change criterion is not satisfied. The change criterion is not satisfied when device 600 fails to detect a change in the measured pace that exceeds a threshold amount. As illustrated in FIG. 6B, device 600 previously measured swimmer's 620 pace to be 2'20"/100 m. At FIG. 6D, swimmer 620 is still swimming at the same pace. As a result, the change in the measured pace is zero, which does not exceed a threshold amount. When the measured pace is less than the threshold amount, device 600 does not provide a visual notification. In some embodiments, the threshold amounts are determined by the set pace. For example, the change criterion is satisfied only when the measured pace crosses from being below pace, to being at pace (e.g., within a predetermined margin) or above pace (e.g., within a predetermined margin). Device 600 optionally turns off display 602 when no visual notification is displayed to conserve battery. Device 600 optionally forgoes issuing a haptic notification when the viewable criterion is not met.

Figure 6E:
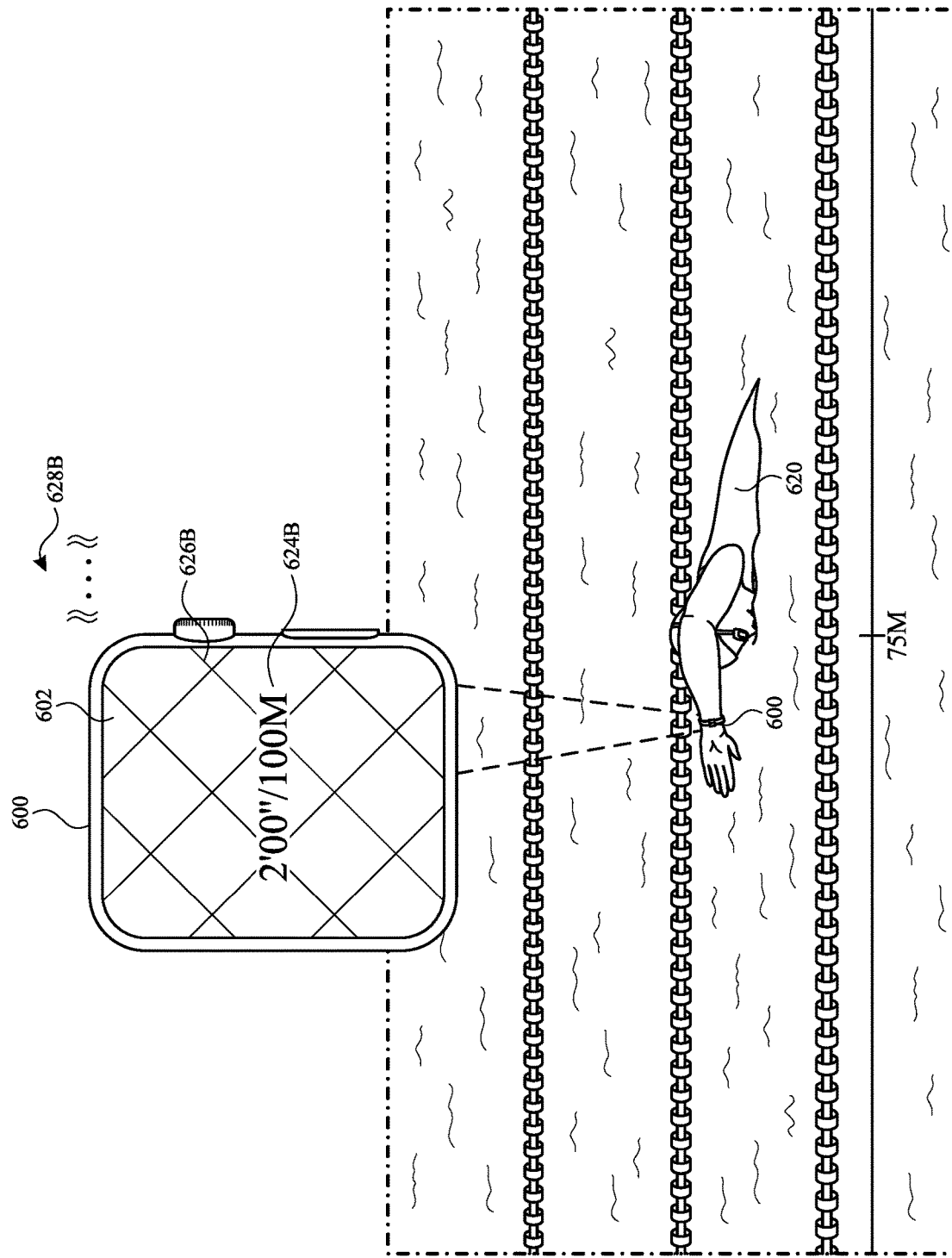

At FIG. 6E, device 600 measures swimmer's 620 increased pace and displays a visual notification 624B that displays text indicating the new, measured pace of swimmer to be 2'00"/100 m, which is the set target pace. Device 600 also displays visual notification 626B, which is a display of a substantially uniform red-green (as denoted by the combination of left-to-right hatching (red) and the right-to-left (green) hatching) color across display 602. In some embodiments, device 600 displays a different color (e.g., blue) indicating the swimmer is swimming at the set target pace. Device 600 illuminates the displayed red-green color at an high level of brightness to make it easier for swimmer 620 to see the notification while swimming. The red-green color of visual notification 626A is selected based on the current swim pace of swimmer 620 being at the target pace set by swimmer 620, as illustrated in FIG. 6A. Device 600 optionally selects the displayed color of visual notification 626B from a gradient of colors between red (e.g., slow pace) and green (e.g., fast pace) that corresponds with the measured pace of swimmer 620. FIG. 6J illustrates that the displayed color may be selected from a gradient of colors between red (slow pace) to green (fast pace) corresponding to the range of paces above and below the set target pace. For example, visual notifications 640A-640E include colors that are selected from a gradient of colors corresponding to the range of measured paces between a slow pace of 2'40" (or more)/100 m to a fast pace of 1'20" (or less)/100 m, where the swimmer set target pace of 2'00"/100 m is in the middle of the range. Device 600 displays visual notification 640A displaying a dark (as denoted by the density of hatching) red color when device 600 detects a significantly slower pace at 2'40"/100 m that is significantly below the set target pace 2'00"/100 m. Device 600 displays visual notification 640B displaying a pace using a light (as denoted by the reduced density of hatching) red when device 600 detects a slightly slower pace of 2'20"/100 m that is slightly slower than the set target pace. Device 600 displays visual notification 640C displaying a blend of greenish-red (e.g., 640C) or different color (e.g., yellow) to indicate swimmer 620 is swimming at the set target pace. Device 600 displays visual notification 640C displaying light green when device 600 measures that swimmer 620 is swimming slightly above the average pace at 1'40"/100 m. Device 600 displays visual notification 640C displaying a dark green color when swimmer 620 is swimming significantly above the average pace at 2'00"/100 m. The display of color in the visual notification provides a more efficient notification interface, as the color of notification 626A lets swimmer 620 know what swimmer's 620 pace is without requiring swimmer 620 to stop and interact with the notification to obtain the swim pace.

Device 600 displays a visual notification 624B and/or 626B when device 600 determines that (visual) notification criteria are met. Notification criteria includes a change criterion. The change criterion is satisfied when device 600 detects that the measured pace differs from the previously measured pace by a threshold amount. For example, device 600 measures the current pace as 2'00"/100 m as swimmer reaches 75 m. The current pace is faster than the previously measured pace of 2'20"/100 m by 20"/100 m. Device 600 displays a visual notification when the change in pace exceeds a set threshold amount (e.g., 5"/100 m). Device 600 also determines that the notification criteria is satisfied because the viewable criterion is satisfied.

Device 600 also issues a haptic notification 626B when notification criteria are met. The frequency of the taps indicates whether swimmer 620 is swimming above pace, below pace or at the target pace. Device 600 issues two taps at a medium frequency (e.g., less delay between taps in comparison to the tap frequency of haptic notification 626A) to indicate swimmer is swimming at the target pace. FIG. 6J illustrates that device 600 issues a two taps at a lower frequency in haptic notification 650A when swimmer 620 is swimming below pace. When swimmer 620 is swimming at the target pace, device 600 issues two taps at a default frequency, as indicated in haptic notification 650B. Device 600 issues a haptic notification 650C comprising two taps at a high frequency when swimmer 620 is swimming above pace. Device 600 optionally increases the intensity of the tap with respect to the pace of the swimmer 620. For example, as swimmer 620 swims at a faster pace, device 600 issues a higher number of taps at higher frequency and a higher intensity. Device 600 issues a lower number of taps at a lower frequency (e.g., more delay between taps) and at a lower intensity. In some embodiments, the visual and haptic notifications are issued concurrently, resulting in device 600 displaying both text and color at the same time as issuing a haptic tap pattern.

Figure 6F:
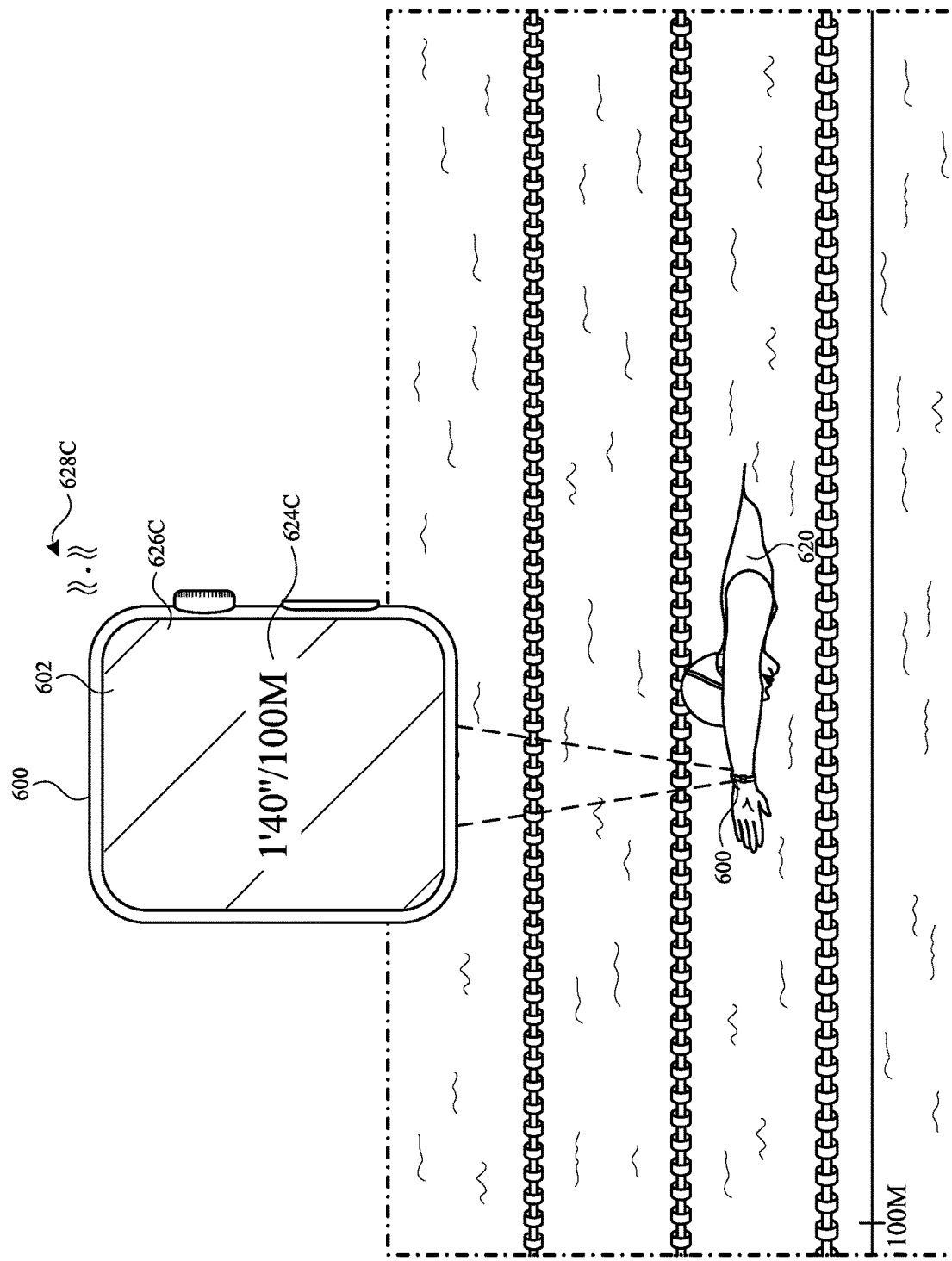

FIG. 6F illustrates device 600 issuing visual notifications 624C, 626C as swimmer continues swimming across the pool when notification criteria are satisfied. Device 600 determines that the new, measured pace 1'40"/100 m is faster than the set target pace of 2'00"/100 m, thereby satisfying the change criterion. Visual notification 624C includes a display of text that reflects the new pace 1'40"/100 m measured by device 600. Device 600 displays visual notification 626C which includes a display of a substantially green color (as denoted by the right-to-left hatching) across display 602 of device 600 because the measured pace is faster than the target pace. In some embodiments, the color displayed in the visual notification 626C is selected from a range of green gradient colors that correspond to paces faster than the target pace.

Device 600 issues a haptic notification 628C when (haptic) notification criteria are satisfied. Device 600 determines that the measured pace is faster than the set target pace. Accordingly, device 600 issues a haptic notification 628C including two taps at a high frequency to indicate that the pace is above target. The frequency of the taps of haptic notification 628C is much higher than the frequency of the taps of haptic notification 628B, which indicates a pace below target.

Figure 6G:
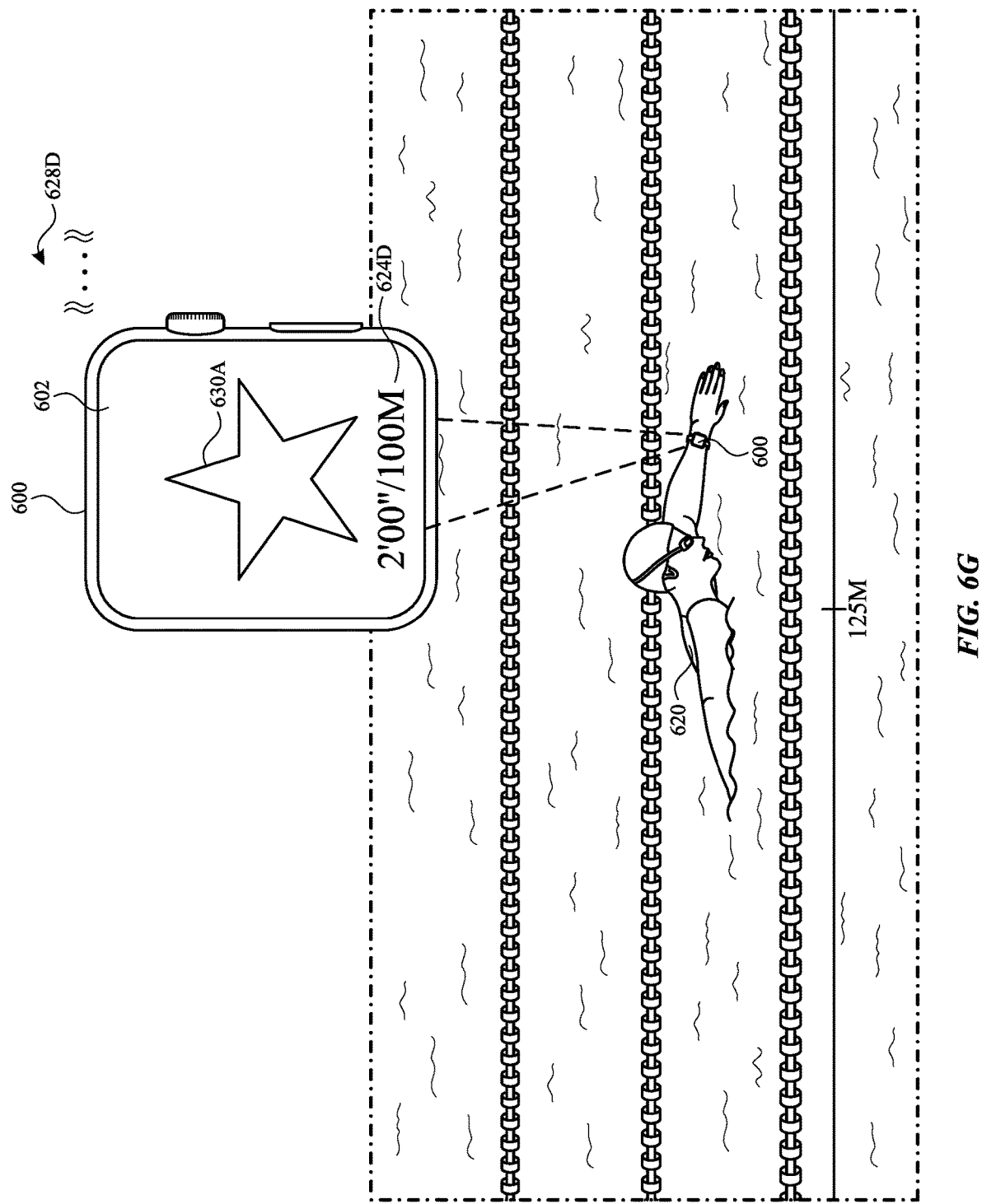
Figure 6H:
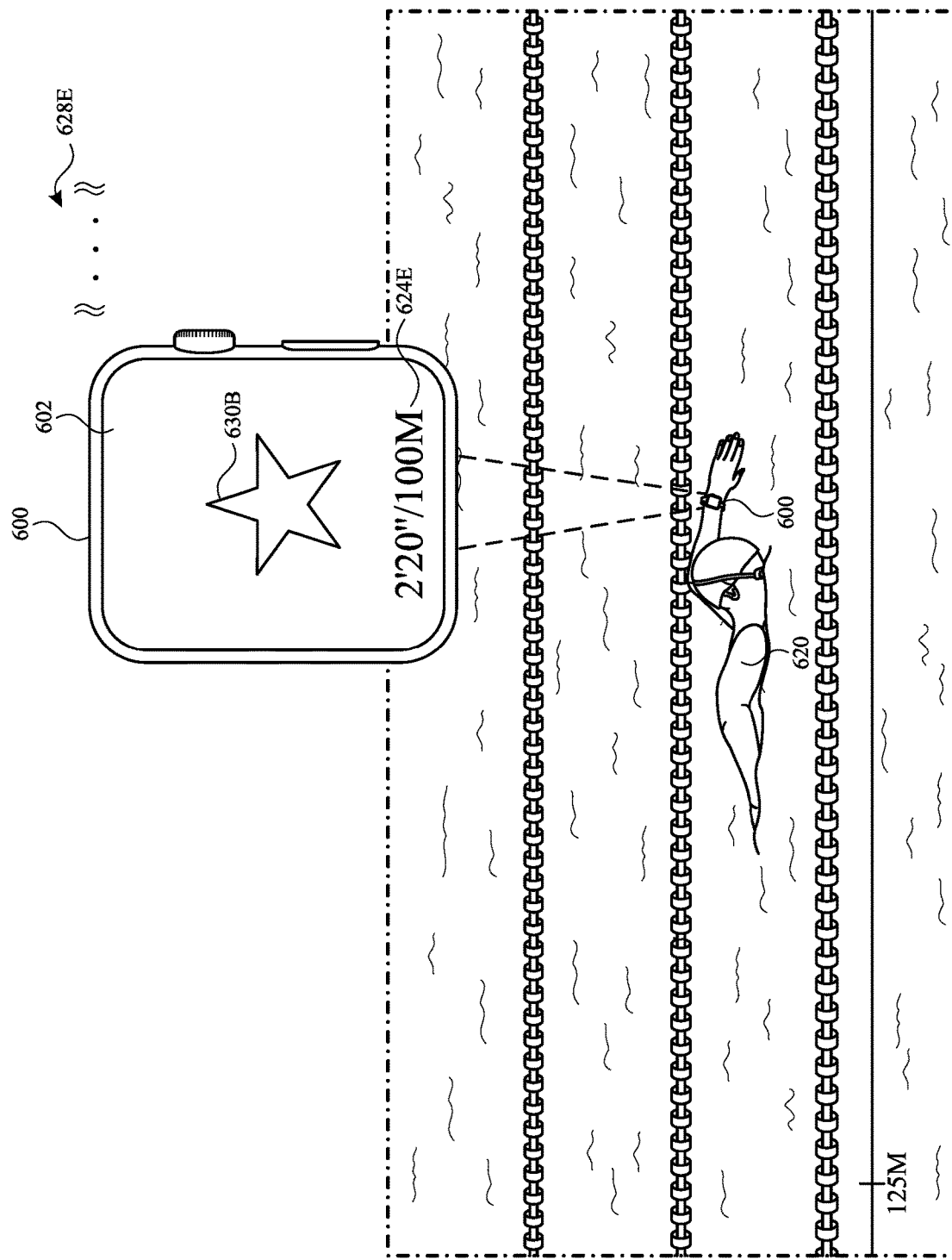

FIGS. 6G-6H illustrates device 600 issuing visual notifications where a star shape is displayed and the size (e.g., a perceptual value of the notification) of the star indicates the measured pace. A smaller sized shape indicates the swimmer is swimming below pace, while a larger sized shape indicates the swimmer is swimming above pace. When device 600 detects a measured pace is the target pace, device 600 issues a visual notification 630A that includes a medium-sized star. When device 600 detects the measured pace is below target, visual notification 630B includes a small star. In some embodiments visual notifications 630A and 630*b* are overlaid over visual notifications that include a display of color and/or text. Device 600 also issues haptic notifications 628D and 6268E respectively that may be issued concurrently with the visual notifications 630A and 630B.

Figure 6I:
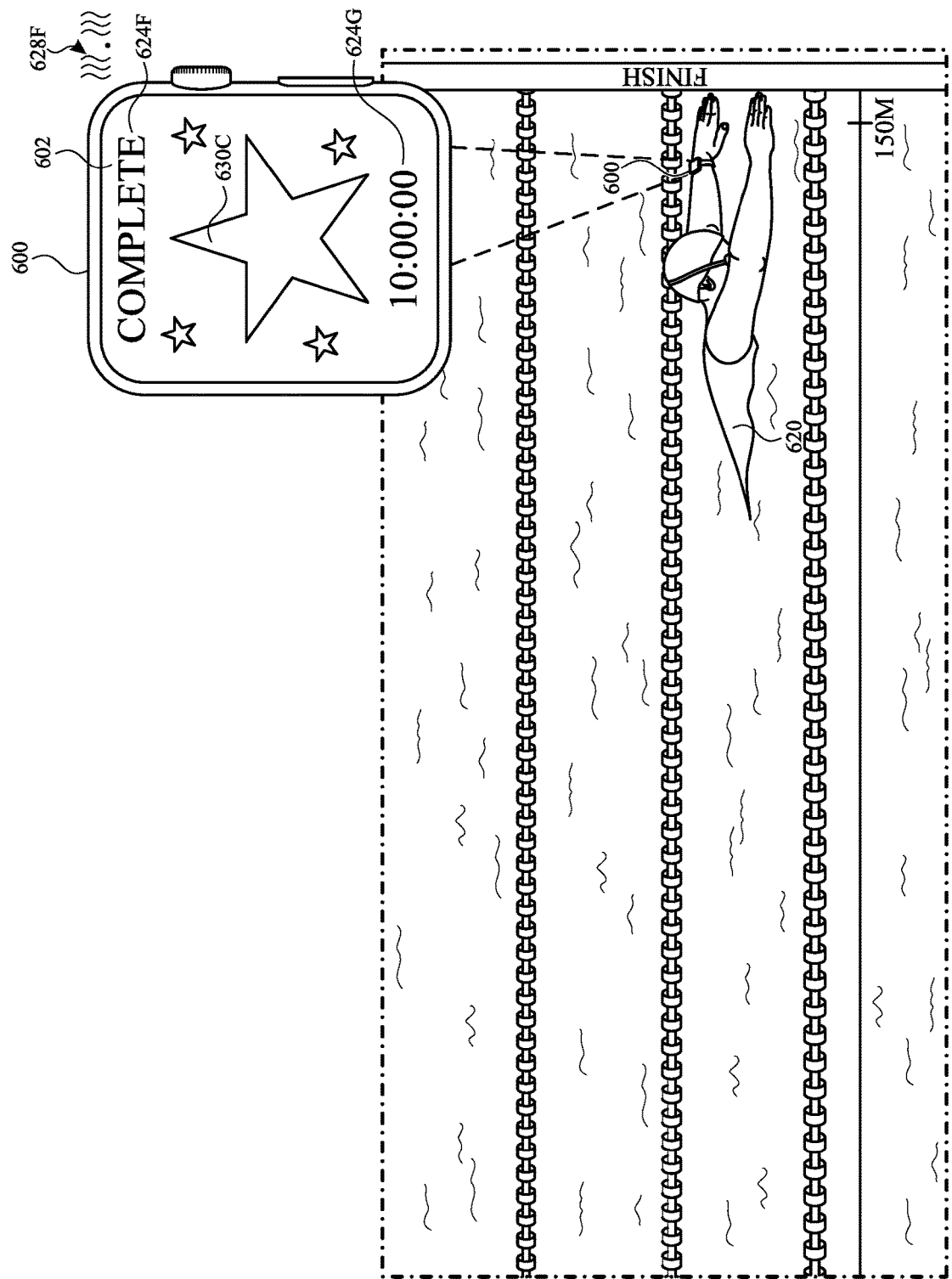
Figure 6J:
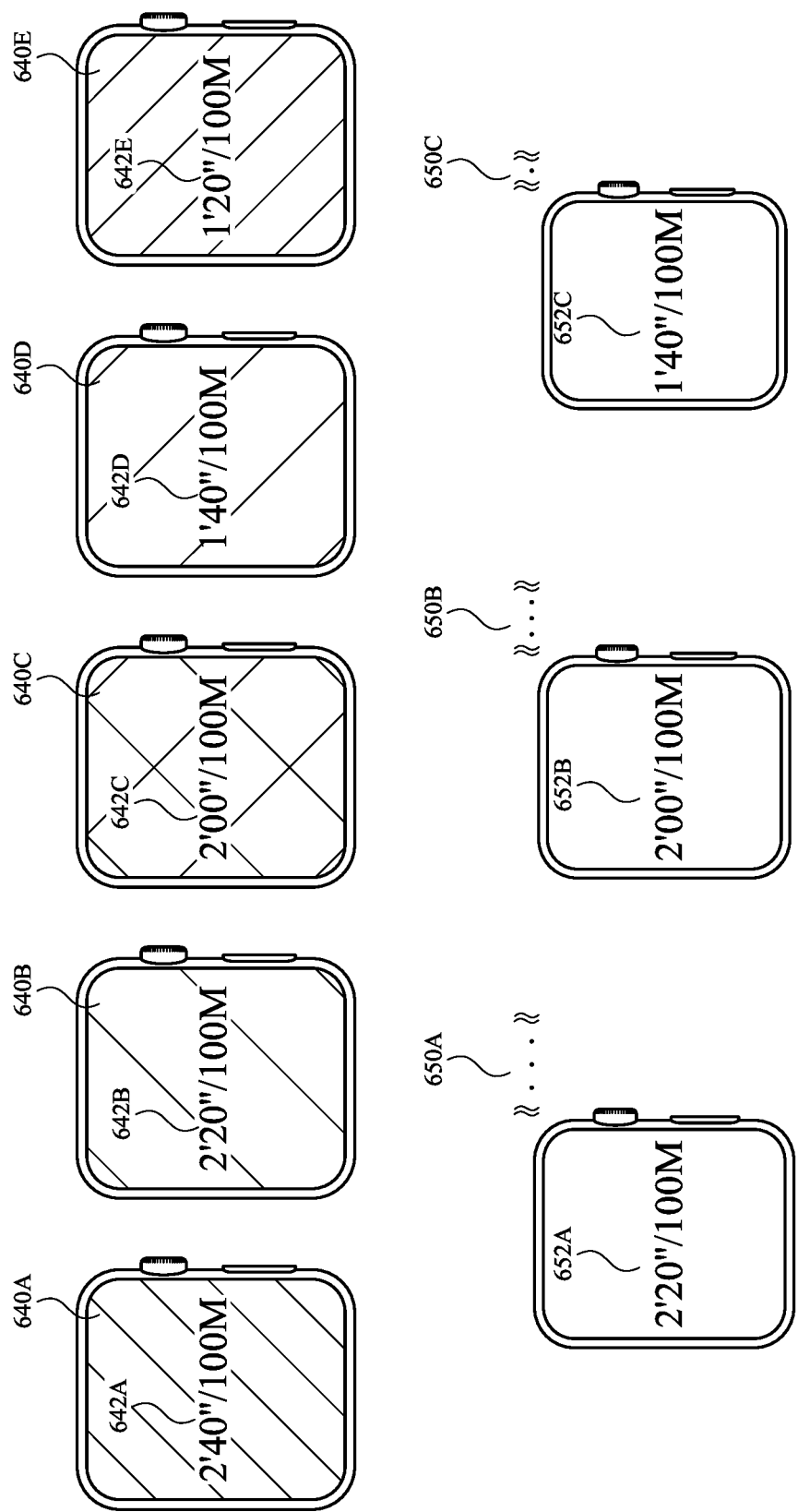

FIG. 6I illustrates electronic device 600 issuing a visual notification that indicates when the swim work out is complete or a goal has been achieved. The completion notification criteria are satisfied when a completion criterion is met by swimmer 620 swimming a target distance, a target number of laps, reaching a target number of calories. Device 600 issues a visual notification 630C that includes a static value such as series of stars indicating the completion of a goal, where the static value is not based on a measured pace. Device 600 displays visual notification 624F including text indicating the completion of a goal and optionally a summary of the measured values such as the total distance swum, the total number of laps swum, the total swim time, the average swim pace, and/or the total number of calories burned. Visual notification 626F includes a display of a substantially uniform color (e.g., blue or multi-colored backgrounds) across display 602 that indicates completion of a goal. The color of the notification is not within the color gradient used to indicate a pace or a swim characteristic. In some embodiments visual notifications 624F and 626F are overlaid over notification 630C, so that the text indicating the achievement of a goal is displayed along with the shape over the background color. In some embodiments, visual notification 624G further includes additional text that provides additional information about the completed goal, such as the total distance, total time, or number of laps swam.

Device 600 also issues a haptic notification 628F includes three taps at a frequency that is associated with completion of the goal and the end of the workout. Haptic notification 628F includes three taps at a fast frequency to indicate the completion of the goal and the end of the workout. The number of taps, frequency, and intensity are predetermined static amounts so that they do not correspond to a measured value of a swim characteristic. The visual 630C and haptic notifications 628F contain static values that are associated with completion so that swimmer 620 may easily distinguish between notifications that indicate completion rather than notifications that indicate an update on a measured value of a pace.

In FIGS. 7A-7D, device 700 is worn by swimmer 720 in an open swim. As seen in FIG. 7A-7D, device 700 provides swimmer 720 with notifications relating to directions to navigate through a swim course in the ocean. Device 700 obtains coordinates of the swim course, a start location, a final destination, and/or the locations of various landmarks (e.g., buoys, coves, piers, structures) in the course prior to the start of the open swim workout. Device 700 generates a route for the swim and provides perceptual notifications containing directions during the course of swimmer's 700 swim when swimmer 720 swims off course. In some embodiments, device 700 optimizes a shortest distance route from the starting point to the destination, that also includes reaching all the landmarks (e.g., buoys). In some embodiments, the optimized route is based on water conditions (e.g., the device 700 steers swimmers away from choppy water or strong currents). Swimmer 720 also enters any metrics that swimmer 720 wants to be tracked and receive notifications for during the swim, such as a pace.

Figure 7A:
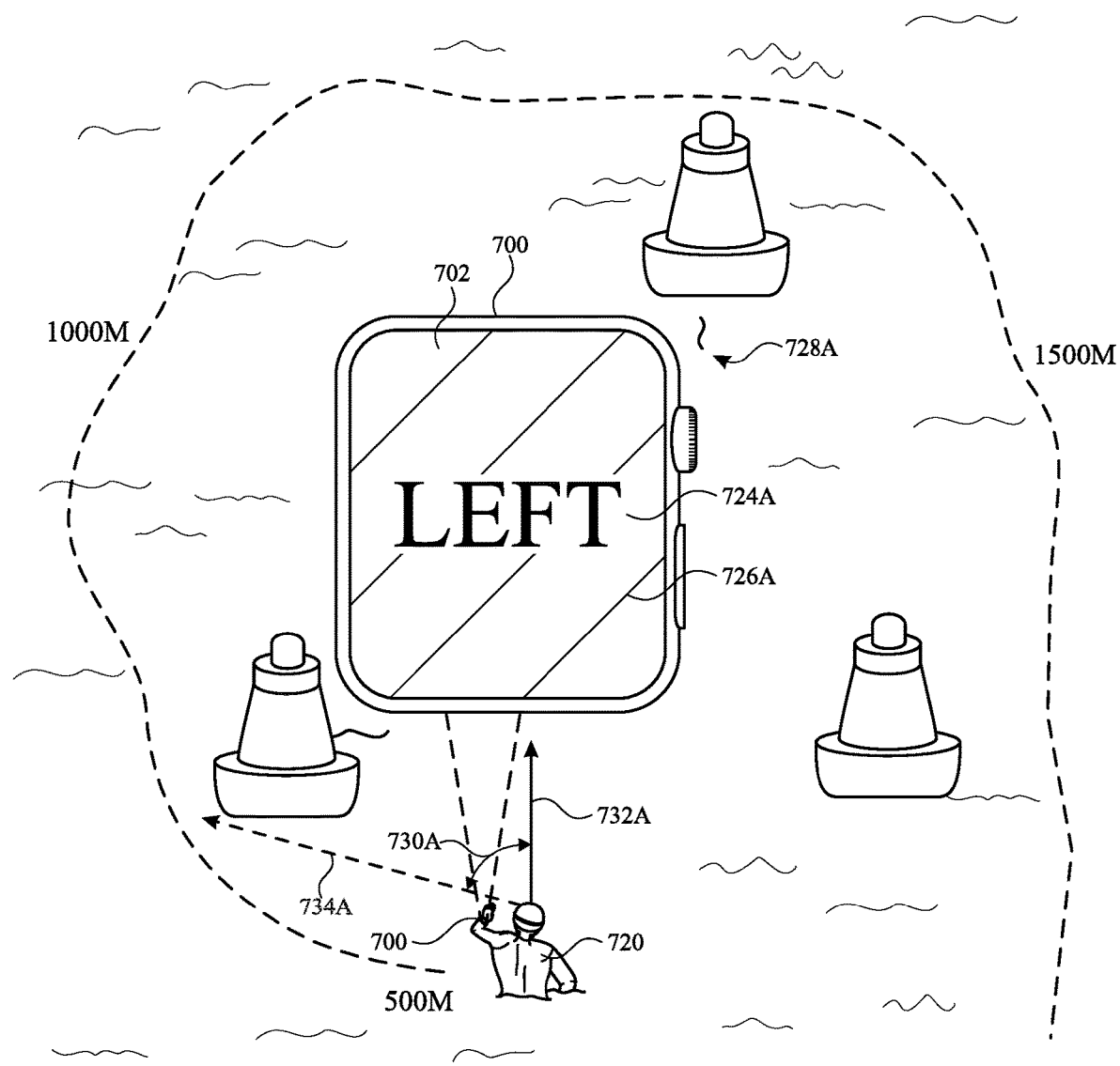
FIGS. 7A-7D illustrate exemplary techniques for providing perceptual notifications to provide directions.
Figure 8A:
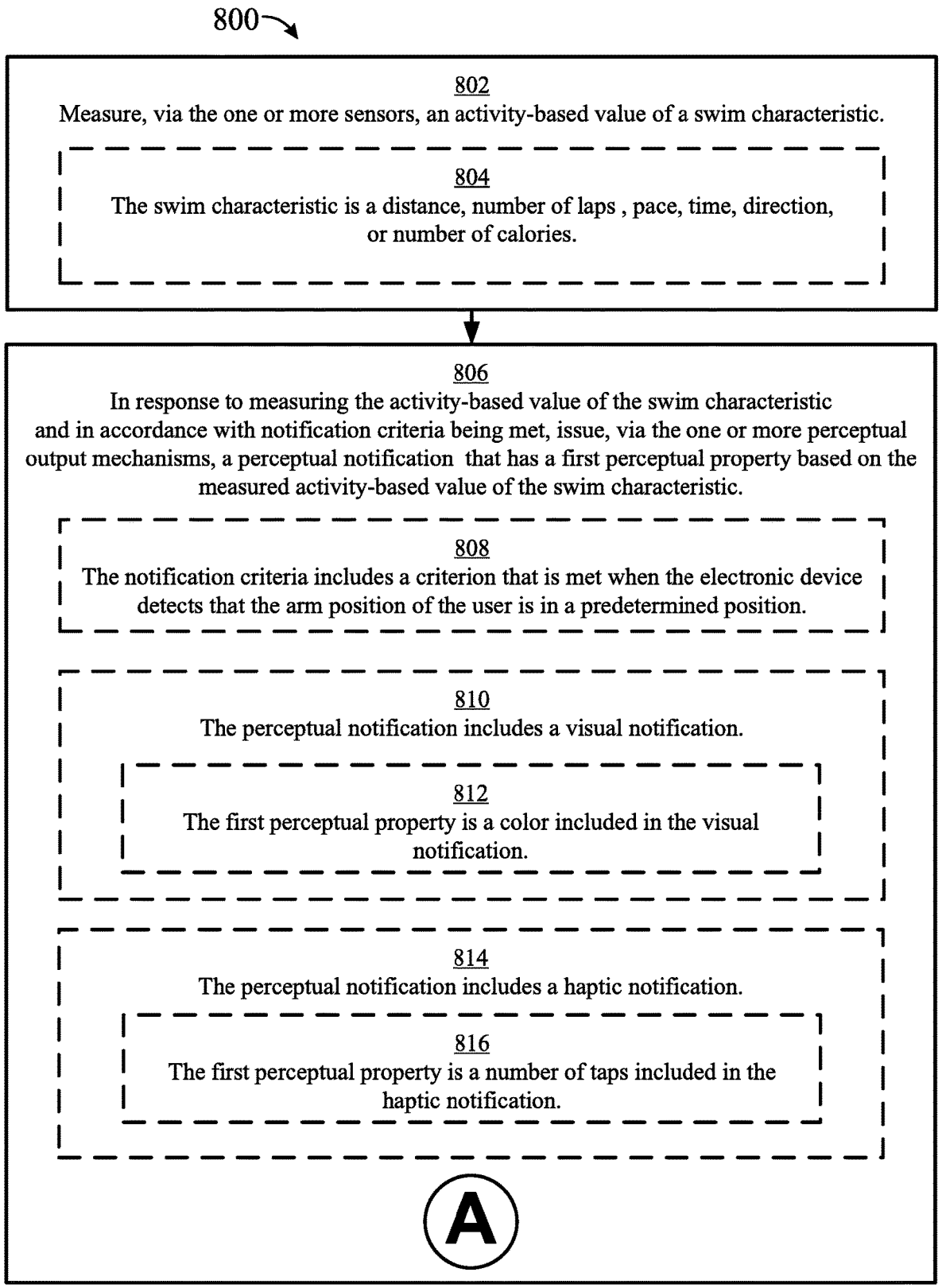

In FIG. 7A, device 700 detects that the current swim direction of swimmer 720 in a north direction. Device 700 determines that the calculated optimal swim route requires swimmer 720 to proceed in the left direction. Device 700 issues a notification 724, 726A, 728A indicating that swimmer 720 should swim in a particular direction when notification criteria are met. Notifications are only displayed when notification criteria are met to conserve battery. In addition to the notification criteria discussed above with respect to FIGS. 6A-6J, notification criteria optionally includes a deviation criterion that is met when device 700 detects that the current swim direction deviates from a target swim direction by more than a non-zero threshold amount. For example, in FIG. 7A, device 700 determines that the current swim direction 732A is north, but target swim direction 734A is to go west. Device 700 determines a deviation angle 730A formed between the current swim direction 732A and target swim direction 734A. When device 700 determines the deviation angle exceeds a first, non-zero, threshold amount (e.g., 30 degrees), the deviation criterion is met. Notification criteria optionally includes a distance criterion that is met when device 700 detects swimmer 720 has swam a predetermined distance (e.g., 25 m-50 m) or a total distance has been swum since the start. For example, swimmer 720 sets perceptual notifications to be displayed every 50 meters. Notification criteria optionally includes a time criterion that is met when device 700 detects a threshold time period has elapsed (e.g., every 10 seconds).

In response to the notification criteria being met, device 700 issues haptic notification 728A. Haptic notification 728A provides a haptic tap pattern that indicates swimmer 730 should swim left from swimmer's 700 current position to stay on course. For example, device 700 issues a haptic notification 728A indicating a left direction by one short tap and a right direction by one long tap. In some embodiments, haptic notification 728A indicates a direction by number of taps: a left direction by one tap and a right direction by three taps. Device 700 optionally increases the frequency of the tap and/or shortens the duration of the tap the further off course swimmer 720 deviates from the target swim direction based on deviation angle 730A. For example, when swimmer 720 deviates from the projected route 734A by a first, non-zero threshold number of degrees (e.g., 30 degrees), device 700 issues a tap at a first frequency. When swimmer 720 deviates from the projected route 734A by a second, non-zero threshold number of degrees (e.g., 90 degrees), where the second threshold is larger than the first threshold, the frequency is increased. In some embodiments, device 700 uses the highest tap intensity to ensure that swimmer 720 feels the haptic notification. In some embodiments, the tap intensity is based on the swimmer's 720 angle of deviation 730A from a target direction 734A. In some embodiments, device 700 uses a combination of the number of taps, frequency, and intensity to indicate the direction in the haptic notification. In some embodiments, device 700 issues directional haptic patterns, where the haptic output is on the left side of device 700 if swimmer 720 should swim left and the haptic output is on the right side of device 700 if swimmer 720 should swim right.

In response to the notification criteria being met, device 700 also issues visual notification 724A that includes text indicating Left to alert swimmer 720 to swim in the left direction from swimmer's 720 current position. In some embodiments, the text displayed includes directions such as left, right, straight, north, east, south, and west. In some embodiments, the text shown in the visual notification gets larger as the angle of deviation 730A increases and exceeds a first threshold and/or a second threshold. Visual notification 726A includes a display of a substantially uniform red color on display 702 of device 700 that indicates the left direction that swimmer 720 should swim in. In some embodiments, device 700 displays a first color (e.g., red) to indicate swimmer 720 should swim left and a second color (e.g., green) to indicate swimmer 720 should swim right. In some embodiments, the color shown in the visual notification 726A gets darker as the angle of deviation 730A increases and exceeds a second threshold. For example, when swimmer 720 has deviated from the target swim direction 734A by more than the second threshold number of degrees, a substantially uniform dark red color is displayed on display 702 to indicate the swimmer should make a sharp left turn. In some embodiments, device 700 displays a first shape of a first size (e.g., small circle) to indicate swimmer 720 should swim left and a second shape of a second size (e.g., small triangle) to indicate swimmer 720 should swim right. The size of the shape changes as the angle of deviation 730A changes. In some embodiments, visual notifications 724A, 726A are a combination of color, text, and shape that represents the direction swimmer 720 should swim in. In some embodiments, device 700 concurrently issues visual notifications 724A, 726A with the haptic notification 728A.

When device 700 is in race mode (e.g., a form of do-not-disturb mode), device 700 optionally suppresses one or more notifications. Iii some embodiments, when device 700 is in race mode, notifications that are not based on a measured value of a swim characteristic are suppressed until device 700 detects that the swim workout has been completed, paused (e.g., taking a break), or ended (e.g., canceled). In some embodiments, if a race mode or do-not-disturb mode is activated on electronic device 620, all notifications including swim-related notifications are suppressed.

Figure 7B:
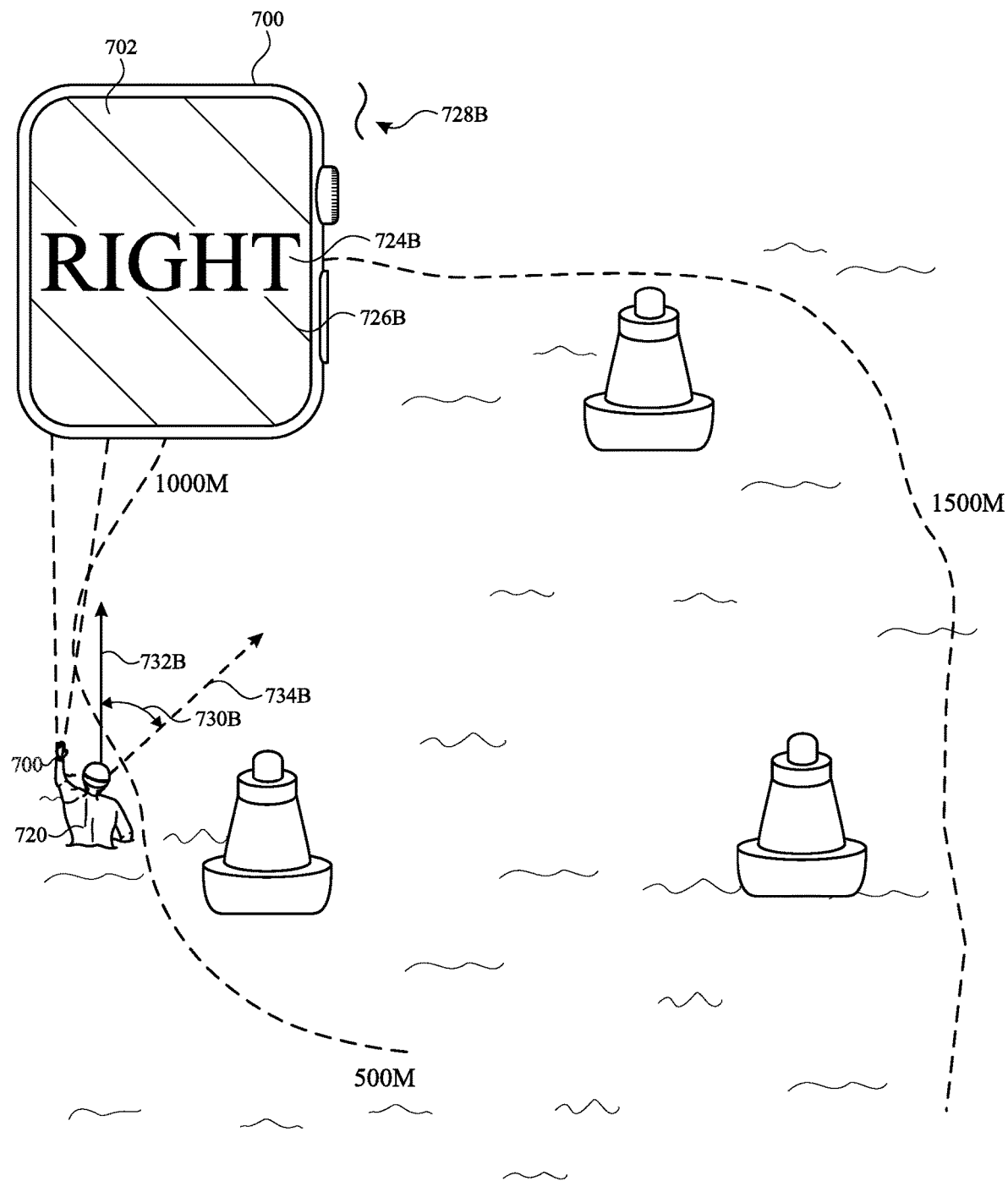

In FIG. 7B, device 700 detects swimmer 720 has drifted off the target swim direction 734B and should swim in the right direction when the angle of deviation 730B exceeds a first threshold number of degrees (e.g., 30 degrees). In response to the notification criteria being met, device 700 issues a haptic notification indicating that swimmer 720 should swim in the right direction. The perceptual notification includes a haptic notification 728C that includes a haptic pattern consisting of one long tap indicating the right direction. In contrast to haptic notification 728A, the haptic pattern for left consists of one short tap.

Device 700 displays visual notifications 724C, 726C when notification criteria are met. The perceptual notification includes a visual notification 724C that includes text indicating that swimmer 720 should go right. Visual notification 726C includes a display of a substantially uniform green color on display 702 indicating swimmer 720 should go right. In some embodiments, the visual notification is a combination of color, text, and shape that represents the direction swimmer 720 should swim in. In some embodiments, the perceptual notification includes issuing visual notifications 724C, 726C concurrently with the haptic notification 728C.

Figure 7C:
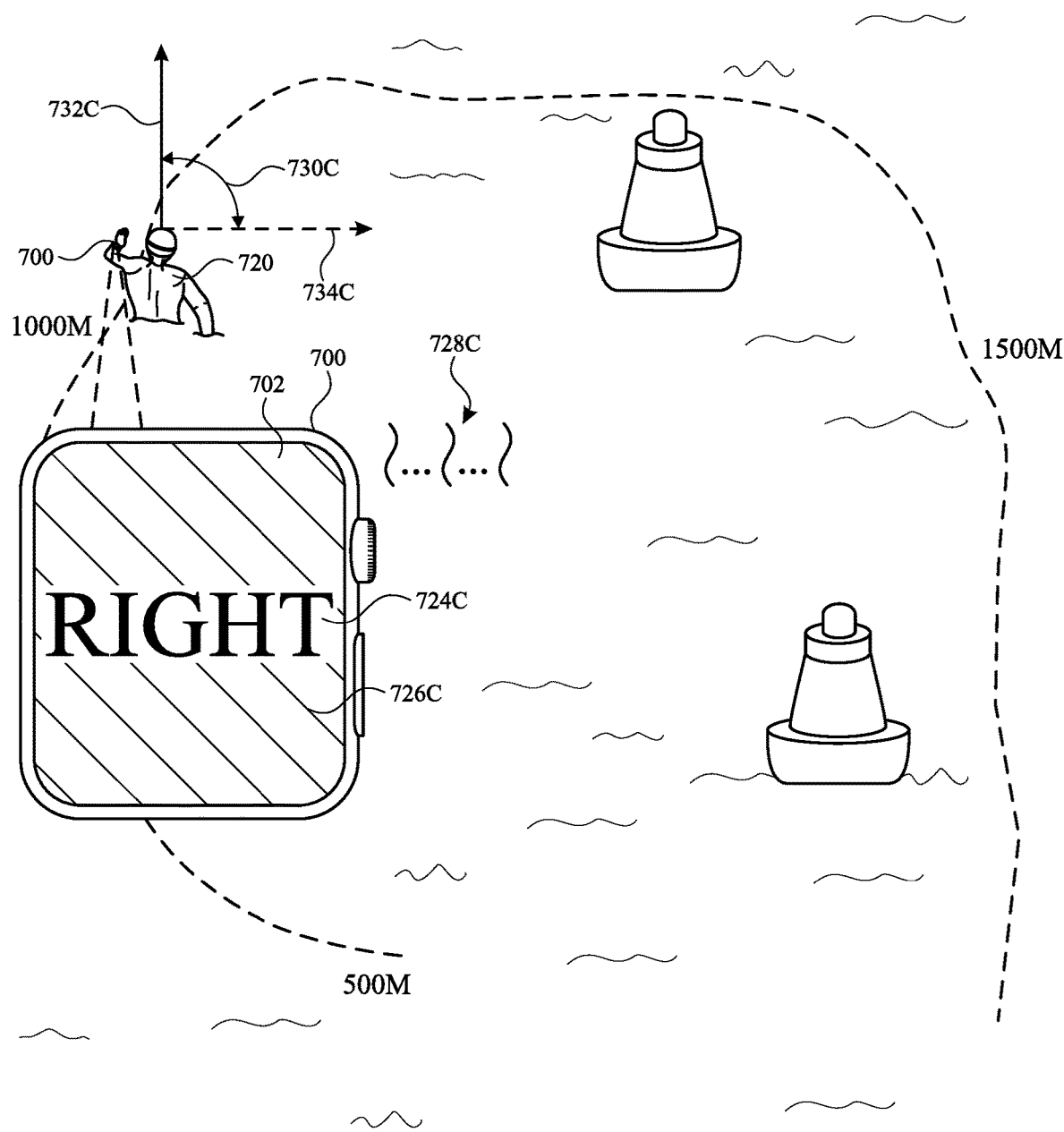

In FIG. 7C, device 700 detects swimmer 720 has continued to veer off the target swim direction 734C and should swim in the right direction to stay on the projected route. Device 700 determines that the swimmer's angle of deviation 730C exceeds a second threshold number of degrees e.g., 90 degrees). In response to the notification criteria being met, device 700 issues a haptic notification 728C that includes a haptic pattern consisting of three, long taps indicating the right direction. The number of taps is increased to inform swimmer 720 that swimmer 720 is more than a second threshold number of degrees off and should make a sharp right turn. In some embodiments, the frequency is optionally increased and/or the duration of the tap is decreased to emphasize how off course swimmer 720 has drifted.

Device 700 displays visual notifications 724C, 726C when notification criteria are met and the viewable criterion is met. Visual notification 724C that includes text indicating swimmer 720 should go right. In some embodiments, device 700 outputs the direction in a larger font size when swimmer 720's angle of deviation 730C exceeds a second threshold number of degrees. Visual notification 726C includes a display of a substantially uniform darker green color indicating swimmer 720 should make a sharper right turn. In some embodiments, visual notifications 724C, 726C are a combination of color, text, and shape that represents the direction swimmer 720 should swim in. In some embodiments, the perceptual notification includes issuing visual notifications 724C, 726C concurrently with haptic notification 728C.

Figure 7D:
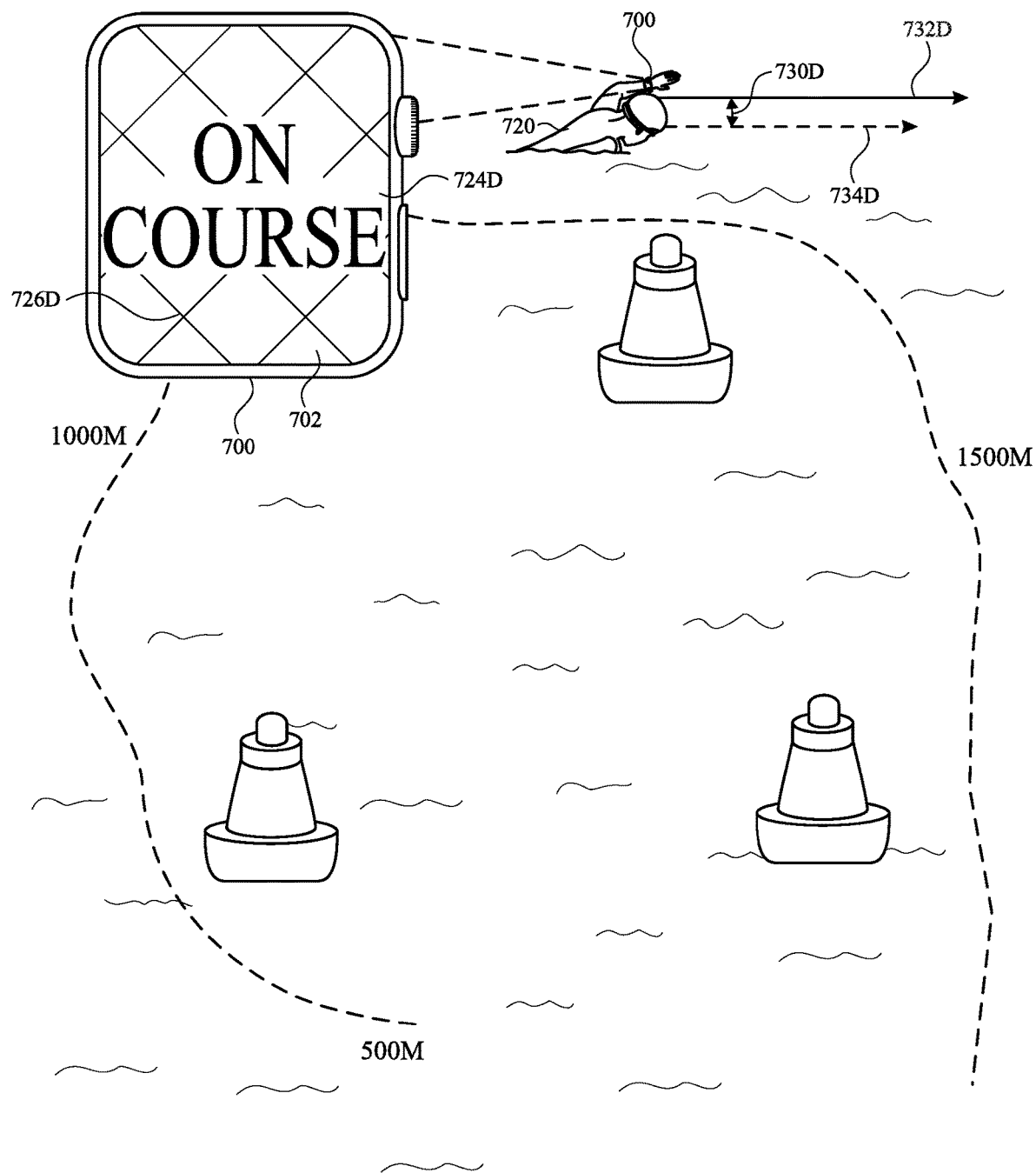

In FIG. 7D, device 700 detects swimmer 720 is swimming on course in the target swim direction 734D. Device 700 determines that swimmer 720's angle of deviation 730D is less than the first threshold number of degrees (e.g., 30 degrees). In response to the notification criteria not being met when no directional correction is needed, device 700 forgoes issuing a visual notification. Device 700 optionally forgoes issuing a haptic notification. In some embodiments, the notification criteria is met when a particular time has elapsed since the swimmer has started swimming or a particular distance has been reached. When no change in direction is detected, electronic device 700 optionally issues a visual notification informing swimmer 720 that he/she is swimming on the projected route 734D.

When device 700 detects that swimmer 720 is on course, device 700 issues visual notifications 724D, 726D when notification criteria are met and the viewable criterion is met. The perceptual notification includes a visual notification 724C that includes text indicating that the swimmer is on course. Visual notification 726C includes a display of a substantially uniform red-green color or a different color (e.g., yellow) indicating swimmer 720 is on course. In some embodiments, visual notifications 724C, 726C are a combination of color, text, and shape that represents the direction swimmer 720 should swim in. In some embodiments, when no directional correction is needed, the perceptual notification includes fewer perceptual properties (e.g., only color, only text, no haptics) than when a directional correction is needed.

FIGS. 8A-8C are flow diagrams illustrating a method for 800 using an electronic device in accordance with some embodiments. Method 700 is performed at a device (e.g., 100, 300, 500, 620, 720) with one or more perceptual output mechanisms and one or more sensors. Some operations in method 800 are, optionally, combined, the orders of some operations are, optionally, changed, and some operations are, optionally, omitted.

As described below, method 800 provides an intuitive way for a measuring activity-based value of a swimming characteristic and presenting the information to the swimmer through a perceptual notification, where the notification has a perceptual property that is based on the measured activity-based value. The method reduces the cognitive burden on a swimmer by presenting measured activity-based values through notifications so that swimmers do not have to stop swimming to get the information in the notification, thereby creating a more efficient human-machine interface. Presenting swimmers with visual or haptic notifications that represent the measured activity-based values provide faster and more efficiently swimmer-device interface that lets the swimmer continue swimming while receiving the information. For battery-operated computing devices, issuing notifications only when notification criteria are met conserves battery.

Electronic device (e.g., 600, 700) with one or more perceptual output mechanisms (e.g., a display; a haptic actuator, an audio speaker) and one or more sensors measures (802), via the one or more sensors, measures an activity-based value of a swim characteristic (e.g., pace, time, distance, and/or direction) (e.g., while a swimmer is swimming).

In some embodiments, the swim characteristic (804) is a distance (e.g., distance remaining, distance travelled), number of laps (e.g., laps completed, laps remaining), pace, (e.g., above or below pace), time (e.g., duration of swim workout, duration left to completion), direction (e.g., for open swim if the swimmer needs to swim left or right to stay on course), or number of calories. In some embodiments, the swim characteristic is a direction of swim and wherein the activity-based value is a measure of the difference (e.g., in degrees, an angle) between a currently detected swim direction (e.g., detected using a GPS, accelerometer, gyroscope, compass) and a target swim direction (e.g., based on GPS determined route, a preset route determined by GPS or by preset by the swimmer).

In response to measuring the activity-based value of the swim characteristic and in accordance with notification criteria being met, electronic device (e.g., 600, 700) issues (806), via the one or more perceptual output mechanisms, a perceptual notification (e.g., 624A, 624B, 624C, 628A) that has a first perceptual property (e.g., color, shape, frequency, intensity, and duration of tap; a non-textual property) based on the measured activity-based value of the swim characteristic. In some examples, the notification criteria includes one or more of: a duration since the last notification (e.g., time duration, a distance duration (e.g., a notification is issued no sooner than once every detected 25 meters swum)) and a change in the measured value that exceeds an activity threshold (e.g., an absolute amount of activity or an amount of change in the activity).

Displaying perceptual notifications that are based on the measured activity-based value of the swim characteristic provides swimmers with real-time swim data without the swimmer having to stop to check the notification. For example, displaying a full screen of color provides information about whether the swimmer is swimming above pace or below pace at a quick glance. Similarly, providing haptic notifications provides the swimmer with real time pace information without the swimmer having to look at the screen. Receiving real-time notifications are useful in notifying the swimmer whether the swimmer is on pace or swimming in the right direction in an open swim, so that the swimmer can make corrections in response to the notification (e.g., swimming faster or turning right). Providing improved notifications to the swimmer without requiting the swimmer to look at the screen or to look at the screen for longer than a quick glance allows the swimmer to obtain swim information by reducing the cognitive burden of the swimmer trying to obtain information while swimming. Providing improved notifications to the swimmer enhances the operability of the device and makes the swimmer-device interface more efficient which, additionally, reduces power usage and improves battery life of the device by enabling the swimmer to use the device more quickly and efficiently.

In some embodiments, the notification criteria includes a criterion that is met when the electronic device (e.g., 600, 700) detects (808) (e.g., via an accelerometer or a gyroscope) that the arm position of the swimmer (e.g., 620, 720) is in a predetermined position (e.g., the predetermined position is a position that corresponds to the electronic device (e.g., 600, 700) being visible during a forward stroke or a stroke where the swimmer's arm position is in front of the swimmer). In some examples, when the predetermined position is a position where electronic device (e.g., 600, 700) is not visible (e.g., the arm is behind the swimmer), electronic device (e.g., 600, 700) forgoes issuing the perceptual notification (e.g., 624A, 624B, 624C, 628A).

Issuing a visual notification when a swimmer's arm position is in a position such that electronic device (e.g., 600, 700) is visible conserves battery power, so that only notifications that are visible to a swimmer are shown. Checking whether the swimmer's arm position is in a predetermined position that corresponds to the swimmer's arm being in front of the swimmer makes the swimmer-device interface more efficient (e.g., only turning on the screen when the display is visible to the swimmer) which, additionally, reduces power usage and improves battery life of the device by enabling the swimmer to use the device more quickly and efficiently.

In some embodiments, the notification criteria includes a criterion that is met when the activity-based value of the swim characteristic is below a first threshold (e.g., a below pace threshold) or when the activity-based value of the swim characteristic is above a second threshold (e.g., an above pace threshold). In some examples, when the change in the activity-based value is not below the first threshold and/or above the second threshold, (e.g., swimming at the same pace), the electronic device (e.g., 600, 700) forgoes issuing a new notification.

In accordance with the measured activity-based value of the swim characteristic having a first measured value (818) (e.g., below pace, deviation from a target direction by more than ten degrees to the right), the first perceptual property has a first perceptual value (e.g., a visual notification that is substantially uniformly red; longer-duration haptic taps).

Displaying perceptual notifications when notification criteria is met when a swim characteristic, such as swimmer's pace is below a first threshold or above a second threshold ensures that notifications are only issued when there's a significant change in the measured activity-based value. For example, when the swim pace changes by a threshold amount or the swimmer is swimming in a direction that is off the target direction by a certain threshold amount triggers a notification to be issued. Providing notifications only when a change in the measured value that exceeds a threshold prevents notifications from constantly being issued and enhances the operability of the device. In addition, the more efficient user interface reduces power usage and improves battery life of the device by enabling the swimmer to use the device more quickly and efficiently.

In accordance with the measured activity-based value of the swim characteristic having a second measured value (824) (e.g., above pace, deviation from a target direction by greater than ten degrees to the left), different than the first measured value, the first perceptual property has a second perceptual value (e.g., a visual notification that is substantially uniformly green; shorter-duration haptic taps), different than the first perceptual value. In some embodiments, the perceptual notification (e.g., 624A, 624B, 624C, 628A, 628B, 628C) includes longer-duration haptic taps to indicate being below pace, shorter-duration haptic taps to indicate being above pace, display red color in full screen to indicate below pace, and green color in full screen to indicate above pace.

In some embodiments, the perceptual notification includes a visual notification (810) (e.g., 624A, 624B, 624C) (e.g., a non-textual notification, a notification that is substantially uniform (e.g., uniform in color and/or intensity) across the display). The first perceptual property is a color included in the visual notification (812). The first perceptual value of the visual notification is a first color (820) (e.g., red if the swimmer is swimming below pace, green if the swimmer is swimming above pace) that corresponds to the first measured value of the swim characteristic; and the second perceptual value is a second color (826) (e.g., red if the swimmer is swimming below pace, green if the swimmer is swimming above pace) that corresponds to the second measured value of the swim characteristic. In some examples, the green color is displayed in full-screen to represent exceeding a pace and red color is displayed in full screen to represent being below pace. In some examples, text or shapes are overlaid on top of the color background in the visual notification.

In some embodiments, the first color and second color are on a gradient (e.g., the gradient of colors includes the range of colors between a first color representing one end of the range of colors and the second color representing the other end of the range of colors) of colors. The method further comprises: in accordance with the measured activity-based value of the swim characteristic having a third measured value, wherein the third measured value is greater than the first measured value and is less than the second value, the third perceptual value is a third color (e.g., the third color is red-green, which is in the middle of the gradient of colors, where the first color is red indicating a slow pace and the second color is green indicating a fast pace), wherein the third color is between the first color and the second color on the gradient (e.g., of the range of colors between the first color and the second color). In some embodiments, the third color may be a dark red is shown if the swimmer is significantly below the average pace, light red is shown if the swimmer is a little below the average pace, light green is shown if the swimmer is a little above the average pace, and dark green is shown if the swimmer is significantly above the average pace.

Visual notifications that display a color representing the measured activity-based value of the swim characteristic provides swimmers with real-time swim data without the swimmer having to stop to check the notification. For example, displaying a full screen of color provides information about whether the swimmer is swimming above pace or below pace at a quick glance. Receiving real-time notifications are useful in notifying the swimmer whether the swimmer is on pace or swimming in the right direction in an open swim, so that the swimmer can make corrections in response to the notification (e.g., swimming faster or turning right). Providing improved notifications to the swimmer without requiring the swimmer to look at the screen or to look at the screen for longer than a quick glance provides a more efficient interface that reduces the cognitive burden on the swimmer. Providing improved notifications to the swimmer enhances the operability of the device and makes the swimmer-device interface more efficient which, additionally, reduces power usage and improves battery life of the device by enabling the swimmer to use the device more quickly and efficiently.

In some embodiments, the perceptual notification includes a visual notification (e.g., 624A, 624B, 624C). The first perceptual property is a shape included in the visual notification. The first perceptual value is a first size of the shape that (e.g., big star or little star) corresponds to the first measured value of the swim characteristic and the second perceptual value is a second size of the shape that corresponds to the second measured value of the swim characteristic. In some embodiments, a large star may represent exceeding a pace and a small star may represent being below pace.

In some embodiments, the perceptual notification includes a haptic notification (814) (e.g., 628A, 628B, 628C) including one or more haptic taps. The first perceptual property is a number of taps included in the haptic notification (816). The first perceptual value of the haptic notification is a first number of taps (822) that corresponds to the first measured value (e.g., a pace, the number of laps left) of the swim characteristic and the second perceptual value is a second number of taps that corresponds to the second measured value (828) (e.g., a pace, the number of laps left) of the swim characteristic. In some examples, a notification comprising a first number of taps indicates that the swimmer is below pace, or the number of laps left to swim. A notification comprising a second number of taps indicates the swimmer is above pace.

In some embodiments, the perceptual notification includes a haptic notification (e.g., 628A, 628B, 628C) including one or more haptic taps. The first perceptual property is a frequency of the one or more haptic taps. The first perceptual value is a first frequency of the one or more haptic taps (e.g., higher frequency of taps indicates faster pace, a lower frequency of taps indicates slower pace) that corresponds to the first measured value (e.g., a pace, the number of laps left) of the swim characteristic and the second perceptual value is a second frequency of the one or more haptic taps that corresponds to the second measured value (e.g., a pace, the number of laps left) of the swim characteristic. In some embodiments, a notification comprising a number of taps at a slow frequency indicates that the swimmer is below pace. A notification comprising a number of taps at a high frequency indicates the swimmer is above pace.

In some embodiments, the perceptual notification includes a haptic notification (e.g., 628A, 628B, 628C) including one or more haptic taps. The first perceptual property is an intensity of the one or more haptic taps. The first perceptual value is a first intensity of the one or more haptic taps (e.g., stronger intensity indicates faster pace, a lower intensity indicates slower pace) that corresponds to the first measured value (e.g., a pace, the number of laps left) of the swim characteristic and the second perceptual value is a second intensity of the one or more haptic taps that corresponds to the second measured value (e.g., a pace, the number of laps left) of the swim characteristic. In some embodiments, a notification comprising a number of taps at a lighter intensity indicates that the swimmer is below pace. A notification comprising a number of taps at a stronger intensity indicates the swimmer is above pace.

Haptic notifications that provide tactile notifications that are based on a measured value of a swim characteristic, such as a pace, without requiring the swimmer to look at the display of the device. For example, outputting a particular number of taps at a particular frequency notifies the swimmer about whether the swimmer is swimming above pace or below pace without having to look at the display. Receiving real-time notifications are useful in notifying the swimmer whether the swimmer is on pace or swimming in the right direction in an open swim, so that the swimmer can make corrections in response to the notification (e.g., swimming faster or turning right). Providing improved notifications to the swimmer without requiring the swimmer to look at the screen provides a more efficient interface that reduces the cognitive burden on the swimmer. Providing improved notifications to the swimmer enhances the operability of the device and makes the swimmer-device interface more efficient which, additionally, reduces power usage and improves battery life of the device by enabling the swimmer to use the device more quickly and efficiently.

In some embodiments, the electronic device (e.g., 600, 700) receives data corresponding to a potential notification (e.g., receiving an incoming email, text message, a trigger condition for an alarm; non-activity-based data; data from an external device). In accordance with a determination that the data corresponding to the potential notification is received while a race mode (e.g., an activity-based do not disturb mode) is not active, electronic device (e.g., 600, 700) issues a perceptual notification (e.g., 624A, 624B, 624C, 628A, 628B, 628C) corresponding to the data (e.g., a visual, audio, or haptic notification). In accordance with a determination that the data corresponding to the potential notification is received while the race mode is active, forgo issuing a perceptual notification (e.g., 624A, 624B, 624C, 628A, 628B, 628C) corresponding to the data.

Note that details of the processes described above with respect to method 800 (e.g., FIGS. 8A-8C) are also applicable in an analogous manner to the methods described above.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to swimmers of measured swim values or any other metrics that may be of interest to swimmers. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a swimmer's health or level of fitness (e.g., vital signs measurements, medication information, exercise information), date of birth, or any other identifying or personal information.

The present disclosure recognizes that the use of such personal information data, in the present technology, can be used to the benefit of swimmers. Further, other uses for personal information data that benefit the swimmer are also contemplated by the present disclosure. For instance, health and fitness data may be used to provide insights into a swimmer's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by swimmers, and should be updated as the collection and/or use of data changes. Personal information from swimmers should be collected for legitimate and reasonable uses of the entity and not shared or sold outside of those legitimate uses. Further, such collection/sharing should occur after receiving the informed consent of the swimmers. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which swimmers selectively block the use of, or access to, personal information data. That is, the present disclosure contemplates that hardware and/or software elements can be provided to prevent or block access to such personal information data. For example, the present technology can be configured to allow swimmers to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a swimmer may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a swimmer's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across swimmers), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. An electronic device, comprising:
   one or more perceptual output mechanisms;
   one or more sensors;
   one or more processors; and
   memory storing one or more programs configured to be executed by the one or more processors, the one or more programs including instructions for:
      measuring, via the one or more sensors, an activity-based value of an activity characteristic;
      in response to measuring the activity-based value of the activity characteristic and in accordance with notification criteria being met, issuing, via the one or more perceptual output mechanisms, a perceptual notification that has a first perceptual property based on the measured activity-based value of the activity characteristic, wherein:
         in accordance with the measured activity-based value of the activity characteristic having a first measured value, the first perceptual property has a first perceptual value; and
         in accordance with the measured activity-based value of the activity characteristic having a second measured value, different than the first measured value, the first perceptual property has a second perceptual value, different than the first perceptual value.

2. The device of claim 1, wherein the activity characteristic is a swim characteristic.

3. The device of claim 2, wherein the swim characteristic is a direction of swim and wherein the activity-based value is a measure of the difference between a currently detected swim direction and a target swim direction.

4. The device of claim 2, wherein the notification criteria includes a criterion that is met when the electronic device detects that the arm position of the swimmer is in a predetermined position.

5. The device of claim 2, wherein the swim characteristic is a distance, number of laps, pace, time, direction, or number of calories.

6. The device of claim 1, wherein:
   the perceptual notification includes a haptic notification including one or more haptic taps;
   the first perceptual property is a number of taps included in the haptic notification;
   the first perceptual value is a first number of taps that corresponds to the first measured value of the activity characteristic; and
   the second perceptual value is a second number of taps that corresponds to the second measured value of the activity characteristic.

7. The device of claim 1, wherein:
   the perceptual notification includes a haptic notification including one or more haptic taps;
   the first perceptual property is a frequency of the one or more haptic taps;
   the first perceptual value is a first frequency of the one or more haptic taps that corresponds to the first measured value of the activity characteristic; and
   the second perceptual value is a second frequency of the one or more haptic taps that corresponds to the second measured value of the activity characteristic.

8. The device of claim 1, wherein:
   the perceptual notification includes a haptic notification including one or more haptic taps;
   the first perceptual property is an intensity of the one or more haptic taps;
   the first perceptual value is a first intensity of the one or more haptic taps that corresponds to the first measured value of the activity characteristic; and
   the second perceptual value is a second intensity of the one or more haptic taps that corresponds to the second measured value of the activity characteristic.

9. The device of claim 1, wherein:
   the perceptual notification includes a visual notification;
   the first perceptual property is a color included in the visual notification;
   the first perceptual value is a first color that corresponds to the first measured value of the activity characteristic; and the second perceptual value is a second color ha corresponds to the second measured value of the activity characteristic.

10. The device of claim 7, wherein the first color and second color are on a gradient of colors, the one or more programs further including instructions for:
in accordance with the measured activity-based value of the activity characteristic having a third measured value, wherein the third measured value is greater than the first measured value and is less than the second value, the third perceptual value is a third color, wherein the third color is between the first color and the second color on the gradient.

11. The device of claim 1, wherein:
the perceptual notification includes a visual notification;
the first perceptual property is a shape included in the visual notification;
the first perceptual value is a first size of the shape that corresponds to the first measured value of the activity characteristic; and
the second perceptual value is a second size of the shape that corresponds to the second measured value of the activity characteristic.

12. The device of claim 1, wherein the notification criteria includes a criterion that is met when the activity-based value of the activity characteristic is below a first threshold or when the activity-based value of the activity characteristic is above a second threshold.

13. The device of claim 1, the one or more programs further including instructions for:
receiving data corresponding to a potential notification;
in accordance with a determination that the data corresponding to the potential notification is received while a race mode is not active, issuing a perceptual notification corresponding to the data; and
in accordance with a determination that the data corresponding to the potential notification is received while the race mode is active, forgo issuing a perceptual notification corresponding to the data.

14. A non-transitory computer-readable storage medium storing one or more programs configured to be executed by one or more processors of an electronic device with one or more perceptual output mechanisms and one or more sensors, the one or more programs including instructions for:
measuring, via the one or more sensors, an activity-based value of an activity characteristic;
in response to measuring the activity-based value of the activity characteristic and in accordance with notification criteria being met, issuing, via the one or more perceptual output mechanisms, a perceptual notification that has a first perceptual property based on the measured activity-based value of the activity characteristic; wherein:
in accordance with the measured activity-based value of the activity characteristic having a first measured value, the first perceptual property has a first perceptual value; and
in accordance with the measured activity-based value of the activity characteristic having a second measured value, different than the first measured value, the first perceptual property has a second perceptual value, different than the first perceptual value.

15. The non-transitory computer-readable storage medium of claim 14, wherein the activity characteristic is a swim characteristic.

16. The non-transitory computer-readable storage medium of claim 15, wherein the swim characteristic is a direction of swim and wherein the activity-based value is a measure of the difference between a currently detected swim direction and a target swim direction.

17. The non-transitory computer-readable storage medium of claim 15, wherein the notification criteria includes a criterion that is met when the electronic device detects that the arm position of the swimmer is in a predetermined position.

18. The non-transitory computer-readable storage medium of claim 15, wherein the swim characteristic is a distance, number of laps, pace, time, direction, or number of calories.

19. The non-transitory computer-readable storage medium of claim 14, wherein:
the perceptual notification includes a haptic notification including one or more haptic taps;
the first perceptual property is a number of taps included in the haptic notification;
the first perceptual value is a first number of taps that corresponds to the first measured value of the activity characteristic; and
the second perceptual value is a second number of taps that corresponds to the second measured value of the activity characteristic.

20. The non-transitory computer-readable storage medium of claim 14, wherein:
the perceptual notification includes a haptic notification including one or more haptic taps;
the first perceptual property is a frequency of the one or more haptic taps;
the first perceptual value is a first frequency of the one or more haptic taps that corresponds to the first measured value of the activity characteristic; and
the second perceptual value is a second frequency of the one or more haptic taps that corresponds to the second measured value of the activity characteristic.

21. The non-transitory computer-readable storage medium of claim 13, wherein:
the perceptual notification includes a haptic notification including one or more haptic taps;
the first perceptual property is an intensity of the one or more haptic taps;
the first perceptual value is a first intensity of the one or more haptic taps that corresponds to the first measured value of the activity characteristic; and
the second perceptual value is a second intensity of the one or more haptic taps that corresponds to the second measured value of the activity characteristic.

22. The non-transitory computer-readable storage medium of claim 14, wherein:
the perceptual notification includes a visual notification;
the first perceptual property is a color included in the visual notification;
the first perceptual value is a first color that corresponds to the first measured value of the activity characteristic; and
the second perceptual value is a second color that corresponds to the second measured value of the activity characteristic.

23. The non-transitory computer-readable storage medium of claim 22, wherein the first color and second color are on a gradient of colors, the one or more programs further including instructions for:
in accordance with the measured activity-based value of the activity characteristic having a third measured value, wherein the third measured value is greater than the first measured value and is less than the second value, the third perceptual value is a third color, wherein the third color is between the first color and the second color on the gradient.

24. The non-transitory computer-readable storage medium of claim 14, wherein:
the perceptual notification includes a visual notification;
the first perceptual property is a shape included in the visual notification;
the first perceptual value is a first size of the shape that corresponds to the first measured value of the activity characteristic; and
the second perceptual value is a second size of the shape that corresponds to the second measured value of the activity characteristic.

25. The non-transitory computer-readable storage medium of claim 14, wherein the notification criteria includes a criterion that is met when the activity-based value of the activity characteristic is below a first threshold or when the activity-based value of the activity characteristic is above a second threshold.

26. The non-transitory computer-readable storage medium of claim 14, the one or more programs further including instructions for:
receiving data corresponding to a potential notification;
in accordance with a determination that the data corresponding to the potential notification is received while a race mode is not active, issuing a perceptual notification corresponding to the data; and
in accordance with a determination that the data corresponding to the potential notification is received while the race mode is active, forgo issuing a perceptual notification corresponding to the data.

27. A method, comprising:
at an electronic device with one or more perceptual output mechanisms and one or more sensors:
measuring, via the one or more sensors, an activity-based value of an activity characteristic;
in response to measuring the activity-based value of the activity characteristic and in accordance with notification criteria being met, issuing, via the one or more perceptual output mechanisms, a perceptual notification that has a first perceptual property based on the measured activity-based value of the activity characteristic, wherein:
in accordance with the measured activity-based value of the activity characteristic having a first measured value, the first perceptual property has a first perceptual value; and
in accordance with the measured activity-based value of the activity characteristic having a second measured value, different than the first measured value, the first perceptual property has a second perceptual value, different than the first perceptual value.

28. The method of claim 27, wherein the activity characteristic is a swim characteristic.

29. The method of claim 27, wherein the swim characteristic is a direction of swim and wherein the activity-based value is a measure of the difference between a currently detected swim direction and a target swim direction.

30. The method of claim 28, wherein the notification criteria includes a criterion that is met when the electronic device detects that the arm position of the swimmer is in a predetermined position.

31. The method of claim 28, wherein the swim characteristic is a distance, number of laps, pace, time, direction, or number of calories.

32. The method of claim 27, wherein:
the perceptual notification includes a haptic notification including one or more haptic taps;
the first perceptual property is a number of taps included in the haptic notification;
the first perceptual value is a first number of taps that corresponds to the first measured value of the activity characteristic; and
the second perceptual value is a second number of taps that corresponds to the second measured value of the activity characteristic.

33. The method of claim 27, wherein:
the perceptual notification includes a haptic notification including one or more haptic taps;
the first perceptual property is a frequency of the one or more haptic taps;
the first perceptual value is a first frequency of the one or more haptic taps that corresponds to the first measured value of the activity characteristic; and
the second perceptual value is a second frequency of the one or more haptic taps that corresponds to the second measured value of the activity characteristic.

34. The method of claim 27, wherein:
the perceptual notification includes a haptic notification including one or more haptic taps;
the first perceptual property is an intensity of the one or more haptic taps;
the first perceptual value is a first intensity of the one or more haptic taps that corresponds to the first measured value of the activity characteristic; and.
the second perceptual value is a second intensity of the one or more haptic taps that corresponds to the second measured value of the activity characteristic.

35. The method of claim 27, wherein:
the perceptual notification includes a visual notification;
the first perceptual property is a color included in the visual notification;
the first perceptual value is a first color that corresponds to the first measured value of the activity characteristic; and
the second perceptual value is a second color that corresponds to the second measured value of the activity characteristic.

36. The method of claim 35, wherein the first color and second color are on a gradient of colors, further comprising:
in accordance with the measured activity-based value of the activity characteristic having a third measured value, wherein the third measured value is greater than the first measured value and is less than the second value, the third perceptual value is a third color, wherein the third color is between the first color and the second color on the gradient.

37. The method of claim 27, wherein:
the perceptual notification includes a visual notification;
the first perceptual property is a shape included in the visual notification;
the first perceptual value is a first size of the shape that corresponds to the first measured value of the activity characteristic; and
the second perceptual value is a second size of the shape that corresponds to the second measured value of the activity characteristic.

38. The method of claim 27, wherein the notification criteria includes a criterion that is met when the activity-based value of the activity characteristic is below a first threshold or when the activity-based value of the activity characteristic is above a second threshold.

39. The method of claim 27, further comprising:
receiving data corresponding to a potential notification;
in accordance with a determination that the data corresponding to the potential notification is received while a race mode is not active, issuing a perceptual notification corresponding to the data; and
in accordance with a determination that the data corresponding to the potential notification is received while the race mode is active, forgo issuing a perceptual notification corresponding to the data.

* * * * *

UNITED STATES PATENT AND TRADEMARK OFFICE
CERTIFICATE OF CORRECTION

PATENT NO. : 10,953,307 B2
APPLICATION NO. : 16/556023
DATED : March 23, 2021
INVENTOR(S) : James R. Wilson et al.

It is certified that error appears in the above-identified patent and that said Letters Patent is hereby corrected as shown below:

In the Claims

In Column 45, Line 1, Claim 9, delete "ha" and insert -- that --, therefor.

In Column 45, Line 52-53, Claim 14, delete "characteristic;" and insert -- characteristic, --, therefor.

In Column 46, Line 38, Claim 21, delete "claim 13," and insert -- claim 14, --, therefor.

In Column 47, Line 57, Claim 29, delete "claim 27," and insert -- claim 28, --, therefor.

In Column 48, Line 30, Claim 34, delete "and." and insert -- and --, therefor.

Signed and Sealed this
Twenty-fifth Day of April, 2023

Katherine Kelly Vidal
*Director of the United States Patent and Trademark Office*